(12) United States Patent
Mandalam et al.

(10) Patent No.: US 9,587,223 B2
(45) Date of Patent: *Mar. 7, 2017

(54) PROTOCOLS FOR MAKING HEPATOCYTES FROM EMBRYONIC STEM CELLS

(71) Applicant: Asterias Biotherapeutics, Inc., Fremont, CA (US)

(72) Inventors: Ramkumar Mandalam, Union City, CA (US); Saadia Faouzi, Daly City, CA (US); Isabelle Nadeau, San Francisco, CA (US); Kristina Pfendler-Bonham, South San Francisco, CA (US); Namitha Rao, San Jose, CA (US); Melissa K. Carpenter, London, CA (US); Lakshmi Rambhatla, Redwood City, CA (US); Choy-Pik Chiu, Cupertino, CA (US)

(73) Assignee: Asterias Biotherapeutics, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/010,578

(22) Filed: Aug. 27, 2013

(65) Prior Publication Data

US 2014/0106343 A1 Apr. 17, 2014

Related U.S. Application Data

(63) Continuation of application No. 12/277,136, filed on Nov. 24, 2008, now Pat. No. 8,546,139, which is a continuation of application No. 10/810,311, filed on Mar. 26, 2004, now Pat. No. 7,473,555, which is a continuation-in-part of application No. 10/087,142, filed on Mar. 1, 2002, now Pat. No. 7,282,366, which is a continuation-in-part of application No. 10/001,267, filed on Oct. 31, 2001, now Pat. No. 7,256,042, which is a continuation-in-part of application No. 09/872,182, filed on May 31, 2001, now Pat. No. 6,506,574, and a continuation-in-part of application No. PCT/US01/13471, filed on Apr. 26, 2001.

(60) Provisional application No. 60/200,095, filed on Apr. 27, 2000.

(51) Int. Cl.
C12N 5/071 (2010.01)

(52) U.S. Cl.
CPC .......... C12N 5/067 (2013.01); C12N 2500/30 (2013.01); C12N 2500/36 (2013.01); C12N 2500/62 (2013.01); C12N 2501/11 (2013.01); C12N 2501/115 (2013.01); C12N 2501/119 (2013.01); C12N 2501/12 (2013.01); C12N 2501/13 (2013.01); C12N 2501/148 (2013.01); C12N 2501/155 (2013.01); C12N 2501/23 (2013.01); C12N 2501/33 (2013.01); C12N 2501/335 (2013.01); C12N 2501/385 (2013.01); C12N 2501/39 (2013.01); C12N 2502/13 (2013.01); C12N 2503/02 (2013.01); C12N 2506/02 (2013.01); C12N 2533/90 (2013.01); C12N 2533/92 (2013.01)

(58) Field of Classification Search
CPC C12N 2503/02; C12N 5/067; C12N 2506/02; C12N 5/0672
See application file for complete search history.

(56) References Cited

U.S. PATENT DOCUMENTS

| | | | |
|---|---|---|---|
| 5,030,105 A | 7/1991 | Kuri-Harcuch et al. |
| 5,532,156 A | 7/1996 | Talbot et al. |
| 5,559,022 A | 9/1996 | Naughton et al. |
| 5,576,207 A | 11/1996 | Reid et al. |
| 5,763,255 A | 6/1998 | Swiderek et al. |
| 5,869,243 A | 2/1999 | Jauregui et al. |
| 6,017,760 A | 1/2000 | Jauregui et al. |
| 6,129,911 A | 10/2000 | Faris |
| 6,458,589 B1 | 10/2002 | Rambhatla et al. |
| 6,506,574 B1 | 1/2003 | Rambhatla et al. |
| 7,186,553 B1 | 3/2007 | Nanba et al. |
| 7,256,042 B2 | 8/2007 | Rambhatla et al. |
| 7,282,366 B2 | 10/2007 | Rambhatla et al. |
| 7,473,555 B2 | 1/2009 | Mandalam et al. |
| 2002/0146678 A1 | 10/2002 | Benvenisty |
| 2003/0138948 A1 | 7/2003 | Fisk et al. |

(Continued)

FOREIGN PATENT DOCUMENTS

| | | |
|---|---|---|
| EP | 0 827 742 | 11/1998 |
| EP | 0 827 743 | 11/1998 |

(Continued)

OTHER PUBLICATIONS

ATCC website info. for Chang liver cells, ATCC # CCL-1, 7 pages (2004).
Webster's Online Dictionary, definition for "HeLa cells," 1 page (1998).
Abe, K. et al., "Endoderm-specific gene expression in embryonic stem cells differentiated to embryoid bodies", Exp. Cell Res. 229(1), 1996, pp. 27-34.
Adams, R. et al., "Effective cryopreservation and long-term storage of primary human hepatocytes with recovery of viability, differentiation, and replicative potential", Cell Transplantation 4(6), 1995, 579-86.

(Continued)

Primary Examiner — Daniel C Gamett
(74) Attorney, Agent, or Firm — Krista P. Kauppinen

(57) ABSTRACT

This disclosure provides a newly developed strategy and particular options for differentiating pluripotent stem cells into cells of the hepatocyte lineage. Many of the protocols are based on a strategy in which the cells are first differentiated into early germ layer cells, then into hepatocyte precursors, and then into mature cells. The cells obtained have morphological features and phenotypic markers characteristic of human adult hepatocytes. They also show evidence of cytochrome p450 enzyme activity, validating their utility for commercial applications such as drug screening, or use in the manufacture of medicaments and medical devices for clinical therapy.

10 Claims, 6 Drawing Sheets

(56) References Cited

U.S. PATENT DOCUMENTS

| | | | |
|---|---|---|---|
| 2005/0037493 | A1 | 2/2005 | Mandalam et al. |
| 2005/0042748 | A1 | 2/2005 | Ochiya et al. |
| 2006/0003446 | A1 | 1/2006 | Keller et al. |
| 2009/0136955 | A1 | 5/2009 | Mandalam et al. |

FOREIGN PATENT DOCUMENTS

| | | |
|---|---|---|
| EP | 0 953 633 | 11/1999 |
| JP | 11-225752 | 8/1999 |
| JP | 2000-14390 | 1/2000 |
| WO | 91/15573 | 10/1991 |
| WO | 95/12665 | 5/1995 |
| WO | 97/47307 | 12/1997 |
| WO | 97/47734 | 12/1997 |
| WO | 99/23885 | 5/1999 |
| WO | 99/37150 | 7/1999 |
| WO | 00/03001 | 1/2000 |
| WO | 00/18239 | 4/2000 |
| WO | 00/22098 | 4/2000 |
| WO | 00/43498 | 7/2000 |
| WO | 00/50048 | 8/2000 |
| WO | 01/39784 | 6/2001 |
| WO | 01/49113 | 7/2001 |
| WO | 01/62901 | 8/2001 |
| WO | 01/81549 | 11/2001 |
| WO | 2005/042703 | 5/2005 |
| WO | 2007/075807 | 7/2005 |
| WO | 2007/002385 | 1/2007 |

OTHER PUBLICATIONS

ATCC, ATCC Catalog information, ATCC No. CRL-1821, Designation ES-E14TG2a, Mus musculus embryo, embryonic stem cell, blastocyst derived, 2010, 3 pages.

ATCC, ATCC catalog information, ATCC No. CRL-1934, designation ES-D3, Mus musculus embryo, strain 129S2/SvPas, pluripotent embryonic stem cell, 2010, 3 pages.

Baribault, H. et al., "Dexamethasone and dimethylsulfoxide as distinct regulators of growth and differentiation of cultured suckling rat hepatocytes", J. Cell Physiol. 129(1), 1986, 77-84.

Block, G. et al., "Population expansion, clonal growth, and specific differentiation patterns in primary cultures of hepatocytes induced by HGF/SF, EGF and TGFÃ_i in a chemically defined (HGM) medium", J. Cell Biol. 132(6), 1996, 1133-49.

Blouin, M. et al., "Specialization switch in differentiating embryonic rat liver progenitor cells in response to sodium butyrate", Exp. Cell Res. 217, 1995, pp. 22-30.

Bluethmann, H. et al., "Establishment of the role of IL-6 and TNF receptor 1 using gene knockout mice", J. Leukoc. Biol. 56, 1994, pp. 565-570.

Bodnar, A. et al., "Extension of life-span by introduction of telomerase into normal human cells", Science 279, 1998, pp. 349-352.

Brill, S. et al., "Expansion conditions for early hepatic progenitor cells from embryonal and neonatal rat livers", Dig Diseases & Sci. 44(2), 1999, 364-71.

Buommino, E. et al., "Sodium butyrate/retinoic acid costimulation induces apoptosis-independent growth arrest and cell differentiation in normal and ras-transformed seminal vesicle epithelial cells unresponsive to retinoic acid", J. Mol. Endocrinol. 24(1), 2000, 83-94.

Cai, J. et al., "Directed Differentiation of Human Embryonic Stem Cells into Functional Hepatic Cells", Hepatology 45, 2007, pp. 1229-1239.

Chen, H-L. et al., "Long-term culture of hepatocytes from human adults", J. Biomed. Sci. 5, 1998, 435-40.

Chen, W. et al., "Reactivation of silenced, virally transduced genes by inhibitors of histone deacetylase", Proc. Natl. Acad. Sci. USA 94, 1997, 5798-803.

Chen, Y-G. et al., "Activin signalling and its role in regulation of cell proliferation, apoptosis, and carcinogenesis", Exp. Biol. Med. 231(5), 2006, pp. 534-544.

Cherny, R. et al., "Strategies for the isolation and characterization of bovine embryonic stem cells", Reprod. Fertil. Dev. 6, 1994, pp. 569-575.

Chinzei, R. et al., "Embryoid-body cells derived from a mouse embryonic stem cell line show differentiation into functional hepatocytes", Hepatol. 36, 2002, 22-9.

Choi, D. et al., "Differentiation of embryonic stem cells into hepatocytes", Tissue Eng. 6(6), 2000, p. 675 Abstract O-43.

Coghlan, A., "Highly cultured", New Scientist 2252:14, 2000.

Coleman, W. et al., "Development of dexamethasone-inducible tyrosine aminotransferase activity in WB-F344 rat liver epithelial stemlike cells cultured in the presence of sodium butyrate", J. Cell Physiol. 161(3), 1994, 463-9.

Davis, M. et al., "Involvement of GiÃ_i2 in sodium butyrate-induced erythroblastic differentiation of K562 cells", Biochem. J. 346, 2000, 455-61.

Devereux, T. et al., "DNA methylation analysis of the promoter region of the human telomerase reverse transcriptase (hTERT) gene", Cancer Res. 59, 1999, 6087-90.

Enat, R. et al., "Hepatocyte proliferation in vitro: Its dependence on the use of serum-free hormonally defined medium and substrata of extracellular matrix", Proc. Natl. Acad. Sci. USA 81, 1984, 1411-5.

Engelmann, G. et al., "Effect of sodium butyrate on primary cultures of adult rat hepatocytes", In Vitro Cell. Dev. Biol. 23(2), 1987, 86-92.

Falasca, L. et al., "The effect of retinoic acid on the re-establishment of differentiated hepatocyte phenotype in primary culture", Cell Tissue Res. 293, 1998, 337-47.

Germain, L. et al., "Biliary epithelial and hepatocytic cell lineage relationships in embryonic rat liver as determined by the differential expression of cytokeratins, alpha-fetoprotein, albumin, and cell surface-exposed components", Cancer Res. 48, 1988, 4909-18.

Germain, L. et al., "Promotion of growth and differentiation of rat ductular oval cells in primary culture", Cancer Res. 48(2), 1988, 368-78.

Gillenwater, A. et al., "Effects of sodium butyrate on growth, differentiation, and apoptosis in head and neck squamous carcinoma cell lines", Head Neck 22(3), 2000, 247-56.

Gladhaug, I. et al., "Effects of butyrate on epidermal growth factor receptor binding, morphology, and DNA synthesis in cultured rat hepatocytes", Cancer Res. 48(22), 1988, 6560-4.

Graham, K. et al., "Sodium butyrate induces differentiation in breast cancer cell lines expressing the estrogen receptor", J. Cell Physiol. 136(1), 1988, 63-71.

Granerus, M. et al., "Growth factors and apoptosis", Cell Prolif. 29, 1996, 309-14.

Grisham, J. et al., "Liver stem cells", Stem Cells, 1997, 233-82.

Guixiang, T. et al., "Different effects of cyclic AMP and butyrate on eosinophilic differentiation, apoptosis and bcl-2 expression of a human eosinophilic leukemia cell line, EoL-1", Hematol Oncol. 14(4), 1996, 181-92.

Hamazaki, T. et al., "Hepatic maturation in differentiating embryonic stem cells in vitro", FEBS Lett. 497(1), 2001, 15-9.

Hamazaki, T. et al., "Hepatic maturation in differentiating embryonic stem cells in vitro", FASEB J. 15(5), 2001, p. A1084.

Hay, D. et al., "Efficient differentiation of hepatocytes from human embryonic stem cells exhibiting markers recapitulating liver development in vivo", Stem Cells 26(4), 2008, pp. 894-902.

Hayashi, Y., "Liver enriched transcription factors and differentiation of hepatocellular carcinoma", Meth. Pathol. 52, 1999, 19-24.

Hoshi, H. et al., "Direct analysis of growth factor requirements for isolated human fetal hepatocytes", In Vitro Cell. Dev. Biol. 23(10), 1987, 723-32.

Imamura, T. et al., "Embryonic stem cell-derived embryoic bodies in three-dimensional culture system form hepatocyte-like cells in Vitro and in Vivo", Tissue Eng. 10(11/12), 2004, 1716-24.

Itskovitz-Eldor, J. et al., "Differentiation of human embryonic stem cells into embryoid bodies comprising the three embryonic germ layers", Mol. Med. 6(2), 2000, 88-95.

Jeng, J. et al., "Effects of butyrate and propionate on the adhesion, growth, cell cycle kinetics, and protein synthesis of cultured human gingival fibroblasts", J. Periodontol. 70(12), 1999, 1435-42.

(56) References Cited

OTHER PUBLICATIONS

Kamitani, H. et al., "Regulation of 12-lipoxygenase in rat intestinal epithelial cells during differentiation and apoptosis induced by sodium butyrate", Arch. Biochem. Biophys. 368(1), 1999, 45-55.
Kaneko, Y. et al., "Alteration of differentiation state of human hepatocytes cultured with novobiocin and butyrate", Cancer Res. 50, 1990, 3101-5.
Kobayashi, N. et al., "Establishment of a highly differentiated immortalized human hepatocyte cell line as a source of hepatic function in the bioartificial liver", Transplant. Proc. 32, 2000, 237-41.
Kono, Y. et al., "Extended primary culture of human hepatocytes in a collagen gel sandwich system", In Vitro Cell. Dev. Biol. Animal 33, 1997, 467-72.
Kosugi, H. et al., "Histone deacetylase inhibitors are the potent inducer/enhancer of differentiation in acute myeloid leukemia: a new approach to anti-leukemia therapy", Leukemia 13, 1999, 1316-24.
Koutsovelkidis, I. et al., "Butyrate inhibits and *Escherichia coli*-derived mitogen(s) stimulate DNA synthesis in human hepatocytes in vitro", Prep. Biochem. Biotechnol. 29(2), 1999, 121-38.
Kubo, A. et al., "Development of definitive endoderm from embryonic stem cells in culture", Development 131, 2003, pp. 1651-1662.
Lavon, N. et al., "Differentiation and isolation of hepatic-like cells from human embryonic stem cells", Differentiation 72, 2004, 230-8.
Lavon, N. et al., "Study of hepatocyte differentiation using embryonic stem cells", J. Cell. Biochem. 96, 2005, 1193-202.
Lazaro, C. et al., "Generation of hepatocytes from oval cell precursors in culture", Cancer Res. 58, 1998, 5514-22.
Lee, J-H. et al., "Histone deacetylase activity is required for embryonic stem cell differentiation", Genesis 38, 2004, 32-8.
Li, J. et al., "Mammalian hepatocyte differentiation requires the transcription factor HNF-4alpha", Genes & Dev. 14, 2000, 464-74.
Masuda, T. et al., "Up-regulation of E-cadherin and Ã¢ -catenin in human hepatocellular carcinoma cell lines by sodium butyrate and interferon-alpha," In Vitro Cell. Dev. Biol. Animal 36, 2000, 387-94.
Matsui, T. et al., "Induction of catecholamine synthesis in human neuroblastoma cells by replication inhibitors and sodium butyrate", Brain Res. 843, 1999, 112-7.
McBain, J. et al., "Apoptotic death in adenocarcinoma cell lines induced by butyrate and other histone deacetylase inhibitors", Biochem Pharm. 53, 1997, 1357-68.
Michalopoulos, G. et al., "Morphogenetic events in mixed cultures of rat hepatocytes and nonparenchymal cells maintained in biological matrices in the presence of hepatocyte growth factor and epidermal growth factor", Hepatology 29(1), 1999, 90-100.
Mitaka, T. et al., "Redifferentiation of proliferated rat hepatocytes cultured in L15 medium supplemented with EGF and DMSO", In Vitro Cell Dev. Biol. 29A, 1993, 714-22.
Mitaka, T. et al., "The current status of primary hepatocyte culture", Int. J. Exp. Path. 79, 1998, 393-409.
Moreadith, R. et al., "Gene targeting in embryonic stem cells: the new physiology and metabolism", J. Mol. Med. 75, 1997, 208-16.
Niki, T. et al., "A histone deacetylase inhibitor, trichostatin A, suppresses myofibroblastic differentiation of rat hepatic stellate cells in pimary culture", Hepatology 29(3), 1999, 858-67.
Pack, R. et al., "Isolation, biochemical characterization, long-term culture, and pheotype modulation of oval cells from carcinogen-fed rats", Exp. Cell Res. 204(2), 1993, 198-209.
Pagan, R. et al., "Effects of growth and differentiation factors on the epithelial-mesenchymal transition in cultured neonatal rat hepatocytes", J. Hepatol. 31, 1999, 859-904.
Park, J. et al., "Establishment and maintenance of human embryonic stem cells on STO, a permanently growing cell line", Biol. Reprod. 69, 2003, pp. 2007-2014.
Pease, S. et al., "Isolation of Embryonic Stem (ES) Cells in Media Supplemented with Recombinant Leukemia Inhibitory Factor (LIF)", Dev. Biol. 141, 1990, pp. 344-352.
Pera, M. et al., "Human embryonic stem cells", J. Cell Sci. 113(Pt. 1), 2000, pp. 5-10.
Perez, R. et al., "Sodium butyrate upregulates Kupffer cell PGE2 production and modulates immune function", J. Surg. Res. 78(1), 1998, 1-6.
Perrine, S. et al., "A short-term trial of butyrate to stimulate fetal-globin-gene expression in the beta-globin disorders", N. Engl. J. Med. 328(2), 1993, 81-6.
Perrine, S. et al., "Butyrate derivatives. New agents for stimulating fetal globin production in the beta-globin disorders", Am. J. Pediatr. Hemotol. Oncol. 16(1), 1994, 67-71.
Rambhatla, L. et al., "Generation of hepatocyte-like cells from human embryonic stem cells", Cell Transplantation 12, 2003, 1-11.
Rathjen, P. et al., "Properties and uses of embryonic stem cells: prospects for application to human biology and gene therapy", Reprod. Fertil. Dev. 10, 1998, 31-47.
Reynolds, S. et al., "Differentiation-inducing effect of retinoic acid, difluoromethylornithine, sodium butyrate and sodium suramin in human colon cancer cells", Cancer Lett. 134(1), 1998, 53-60.
Rivero, J. et al., "Sodium butyrate stimulates PKC activation and induces differential expression of certain PKC isoforms during erythroid differentiation", Biochem. Biophys. Res. Comm. 248(3), 1998, 664-8.
Robertson, E., Teratocarcinomas and Embryonic Stem Cells: A Practical Approach, IRL Press, Oxford, Jan. 1, 1987 00:00:00.0, pp. 71-112.
Rocchi, P. et al., "Effect of butyrate analogues on proliferation and differentiation in human neuroblastoma cell lines", Anticancer Res. 18, 1998, 1099-103.
Rogler, L. , "Selective bipotential differentiation of mouse embryonic hepatoblasts in vitro", Am. J. Pathol. 150(2), 1997, 591-602.
Ruhnke, M. et al., "Long-term culture and differentiation of rat embryonic stem cell-like cells into neuronal, glial, endothelial, and hepatic lineages", Stem Cells 21, 2003, 428-36.
Runge, D. et al., "Stat 1 alpha/1 beta, Stat 3 and Stat 5: Expression and Association with c-MET and EGF-Receptor in Long-Term Cultures of Human Hepatocytes", Biochem. Biophys. Res. Comm. 265, 1999, 376-81.
Saito, H. et al., "Changes of antigen expression on human hepatoma cell lines caused by sodium butyrate, a differentiation inducer", J. Gastroenterol. 29, 1994, 733.
Saito, H. et al., "Differentiating effect of sodium butyrate on human hepatoma cell lines PLC/PRF/5, HCC-M and HCC-T", Int. J. Cancer 48(2), 1991, 291-6.
Saito, H. et al., "Effect of dexamethasone, dimethylsulfoxide and sodium butyrate on a human hepatoma cell line PLC/PRF/5", Cancer Biochem. Biophys. 13, 1992, 75-84.
Sanchez, A. , "Transforming growth factor-beta (TGF-beta) and EGF promote cord-like structures that indicate terminal differentiation of fetal hepatocytes in primary culture", Exp. Cell Res. 242, 1998, 27-37.
Schuldiner, M. et al., "Effects of eight growth factors on the differentiation of cells derived from human embryonic stem cells", Proc. Natl. Acad. Sci. USA 97(21), 2000, pp. 11307-11312.
Schultz, R. et al., "Reprogramming of gene expression during preimplantation development", J. Exp. Zool. (Mol. Dev. Evol.) 285:, 1999, 276-82.
Shirahashi, H. et al., "Differentiation of human and mouse embryonic stem cells along a hepatocyte lineage", Cell Transplantation 13, 2004, 197-211.
Siavoshian, S. et al., "Butyrate and trichostatin A effects on the proliferation/differentiation of human intestinal epithelial cells: induction of cyclin D3 and p21 expression", Gut 46(4), 2000, 507-14.
Simon, B. et al., "Transient transcriptional activation of gastrin during sodium butyrate-induced differentiation of islet cells", Regul. Pept. 70, 1997, 143-8.
Soto-Gutierrez, A. et al., "Differentiation of human embryonic stem cells to hepatocytes using deleted variant of HGF and poly-amino-urethane-coated nonwoven polytetrafluoroethylene fabric", Cell Transplantation 15(4), 2006, pp. 335-341.

(56) References Cited

OTHER PUBLICATIONS

Staecker, J. et al., "Sodium butyrate preserves aspects of the differentiated phenotype of normal adult rat hepatocytes in culture", J. Cell. Physiol. 135(3), 1988, 367-76.
Staecker, J. et al., "Stimulation of DNA synthesis in primary cultures of adult rat hepatocytes by sodium butyrate", Biochem. Biophys. Res.Comm. 147(1), 1987, 78-85.
Staecker, J. et al., "The effect of sodium butyrate on tyrosine aminotransferase induction in primary cultures of normal adult rat hepatocytes", Arch. Biochem. Biophys. 261(2), 1988, 291-8.
Strain, A., "Ex vivo liver cell morphogenesis: one step nearer to the bioartificial liver", Hepatology 29(1), 1999, 288-90.
Sun, S. et al., "Altered phospholipid metabolism in sodium butyrate-induced differentiation of C6 glioma cells", Lipids 32(3), 1997273-82.
Tamagawa, K. et al., "Proanthocyanidins from barley bran potentiate retinoic acid-induced granulocytic and sodium butyrate-induced monocytic differentiation of HL60 cells", Biosci. Biotechnol. Biochem.62(8), 1998, 1483-7.
Tanaka, T. et al., "Adenovirus-mediated prodrug gene therapy for carcinoembryonic antigen-producing human gastric carcinoma cells in vitro", Cancer Res. 56(6), 1996, 1341-5.
Tateno, C. et al., "Growth and differentiation of adult rat hepatocytes regulated by the interaction between parenchymal and non-parenchymal liver cells", J. Gast. Hepatol. 13(Suppl.), 1998, S83-92.
Tateno, C. et al., "Growth potential and differentiation capacity of adult rat hepatocytes in vitro", Wound Rep. Reg 7(1), 1999, 36-44.
Thomson, J. et al., "Embryonic stem cell lines derived from human blastocysts", Science 282, 1998, 1145-7.
Thomson, J. et al., "Isolation of a primate embryonic stem cell line", Proc. Natl. Acad. Sci. USA 92, 1995, 7844-8.
Thomson, J. et al., "Neural Differentiation of Rhesus Embryonic Stem Cells", APMIS 106, 19980, pp. 149-156.
Trounson, A. et al., "Potential benfits of cell cloning for human medicine", Reprod. Fertil. Dev. 10, 1998, 121-5.
Verfaillie, C. et al., "Stem Cells: Hype and Reality", Hematology Am. Soc. Hematol. Educ. Program, 2002, pp. 369-391.
Wang, G. et al., "Transforming growth factor-beta 1 acts cooperatively with sodium n-butyrate to induce differentiation of normal human keratinocytes", Exp. Cell Res. 198(1), 1992, 27-30.
Watkins, S. et al., "Butyric acid and tributyrin induce apoptosis in human hepatic tumour cells", J. Dairy Res. 66(4), 1999, 559-67.
Yabushita, H. et al., "Effects of sodium butyrate, dimethylsulfoxide and dibutyryl cAMP on the poorly differentiated ovarian adenocarcinoma cell line AMOC-2", Oncol. Res. 5(4-5), 1993, 173-82.
Yamada, K. et al., "Effects of butyrate on cell cycle progression and polyploidization of various types of mammalian cells", Biosci. Biotechnol. Biochem. 56(8), 1992, 1261-5.
Yoon, J-H. et al., "Augmentation of Urea-synthetic Capacity by Inhibition of Nitric Oxide Synthesis in Butyrate-Induced Differentiated Human Hepatocytes", FEBS Lett. 474, 2000, 175-8.
Yoon, J-H. et al., "Development of a non-transformed human liver cell line with differentiated-hepatocyte and urea-synthetic functions: applicable for bioartificial liver", Int. J. Artifical Organs 22(11), 1999, 769-77.
Yoshizawa, T. et al., "Dimethylsulfoxide maintains intercellular communication by preserving the gap junctional protein connexin32 in primary cultured hepatocyte doublets from rats", J. Gastroenterol Hepatol. 12, 1997, 325-30.
Zaret, Kenneth S., "Hepatocyte Differentiation: from the endoderm and beyond", Curr. Op. Genet. Dev. 11, 2001, 568-74.
Zvibel, I. et al., "Phenotypic characterization of rat hepatoma cell lines and lineage-specific regulation of gene expression by differentiation agents", Differentiation 63, 1998, 215-23.

Figure 1
Staged Butyrate Protocol
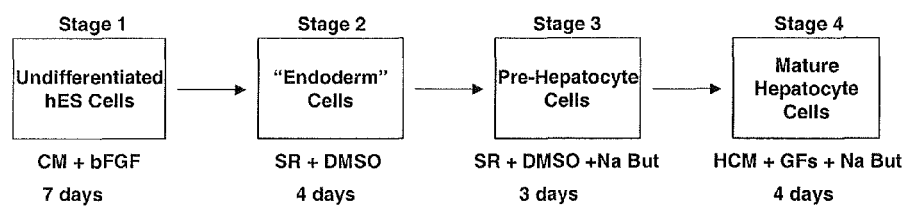
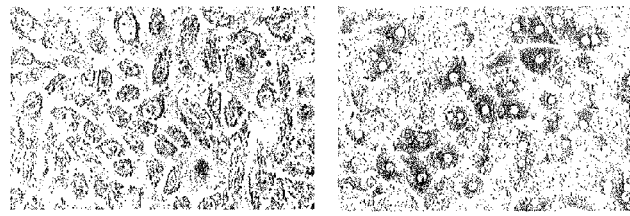
PSC Derived Hepatocytes     Adult Hepatocytes
hESC Derived Hepatocyte-like Cells
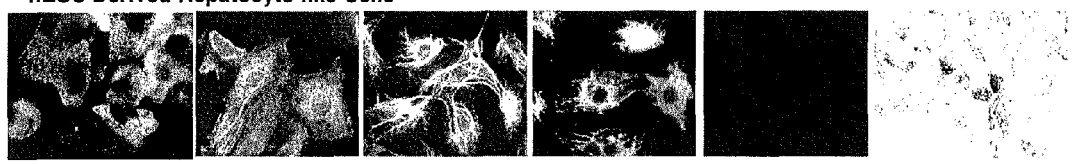
Adult Human Hepatocytes
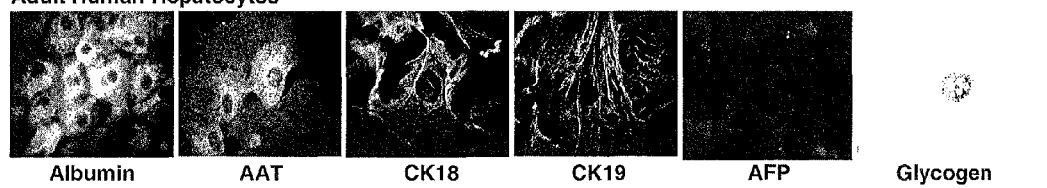
Albumin     AAT     CK18     CK19     AFP     Glycogen

Figure 2
Serum Replacement + DMSO Protocol
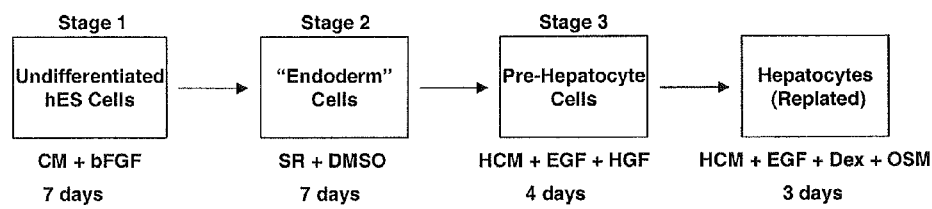
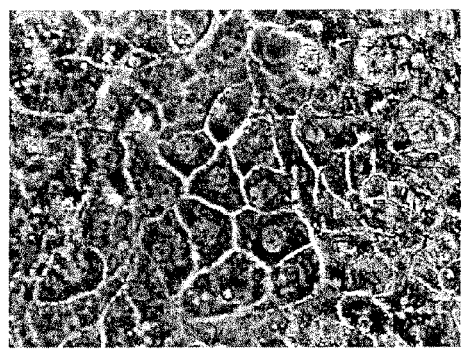
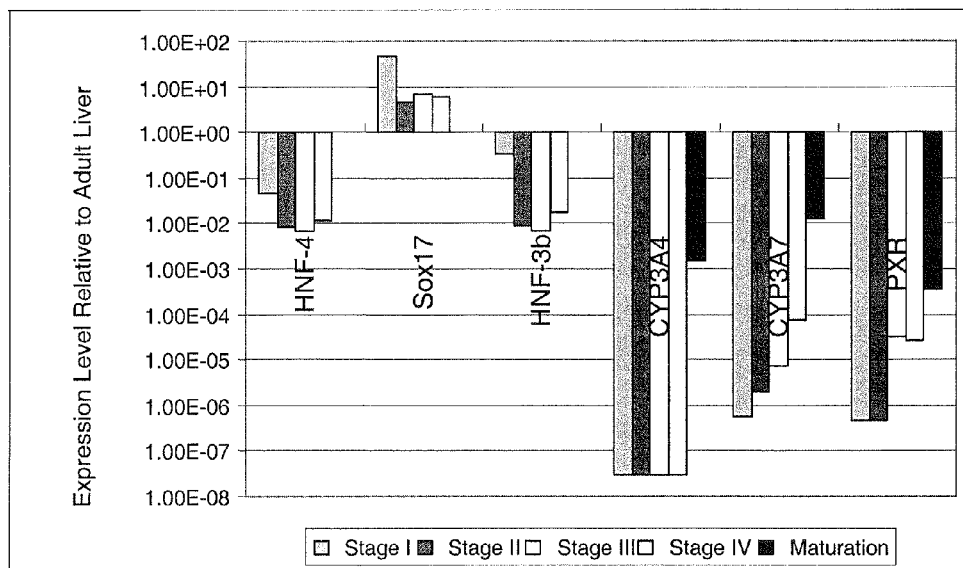

Figure 3

Growth Factor Protocol

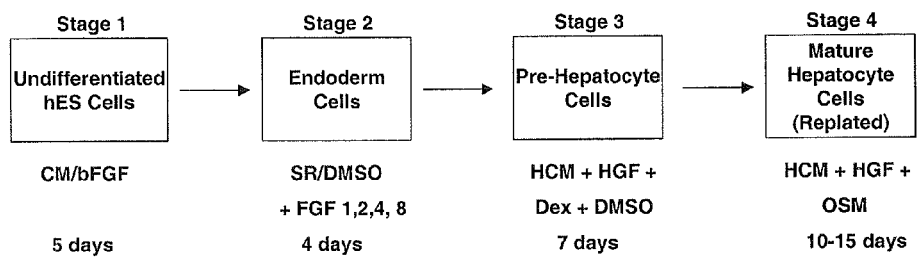

| Stage 1 | Stage 2 | Stage 3 | Stage 4 |
|---|---|---|---|
| Undifferentiated hES Cells | Endoderm Cells | Pre-Hepatocyte Cells | Mature Hepatocyte Cells (Replated) |
| CM/bFGF | SR/DMSO + FGF 1,2,4, 8 | HCM + HGF + Dex + DMSO | HCM + HGF + OSM |
| 5 days | 4 days | 7 days | 10-15 days |

Endoderm Protocol

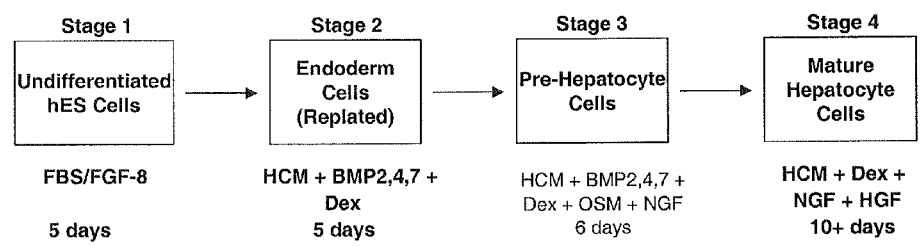

| Stage 1 | Stage 2 | Stage 3 | Stage 4 |
|---|---|---|---|
| Undifferentiated hES Cells | Endoderm Cells (Replated) | Pre-Hepatocyte Cells | Mature Hepatocyte Cells |
| FBS/FGF-8 | HCM + BMP2,4,7 + Dex | HCM + BMP2,4,7 + Dex + OSM + NGF | HCM + Dex + NGF + HGF |
| 5 days | 5 days | 6 days | 10+ days |

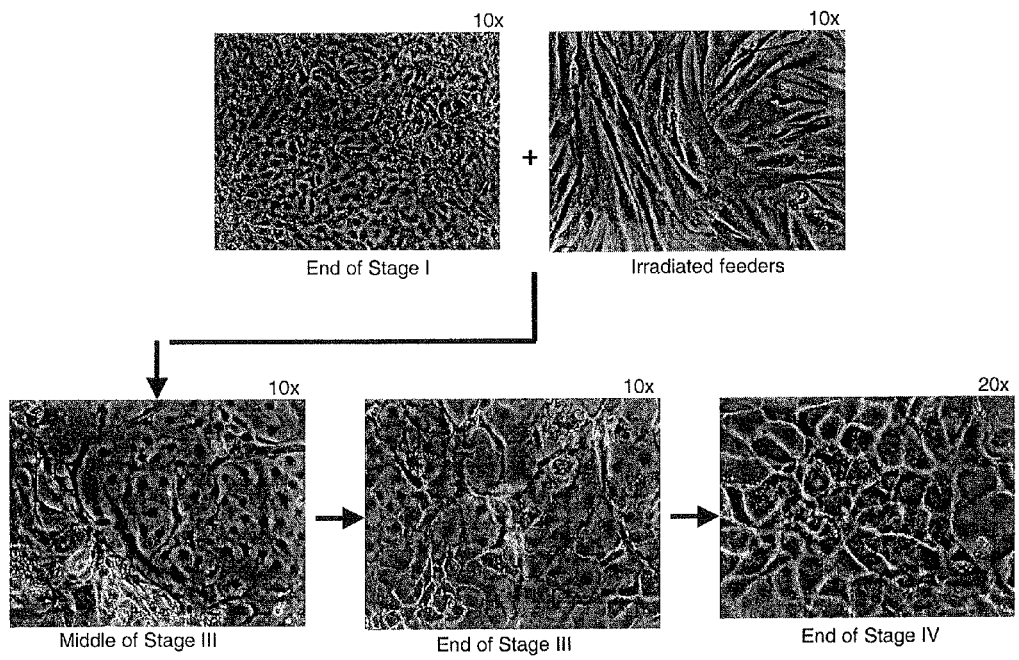

Figure 4
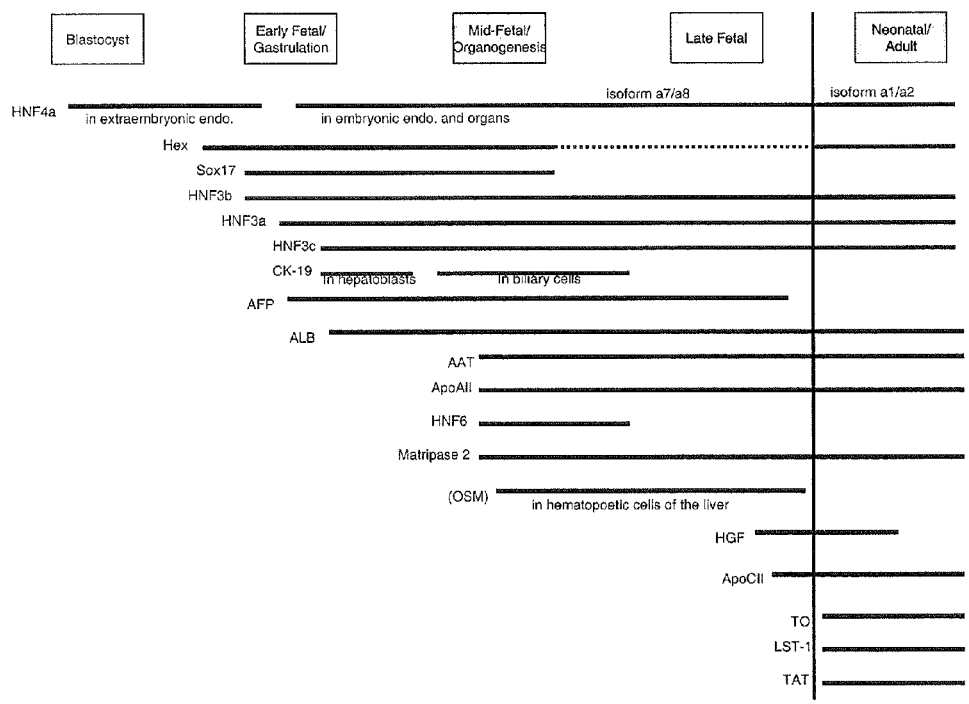
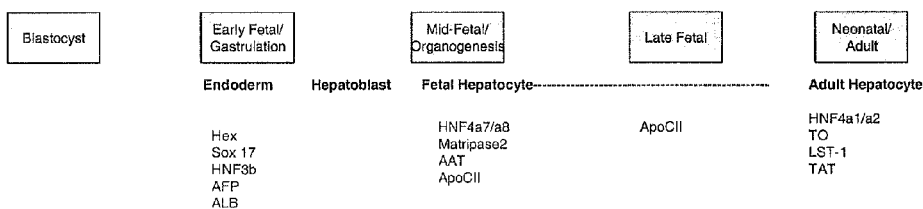

Figure 5
Expression of Liver Markers by RT-PCR
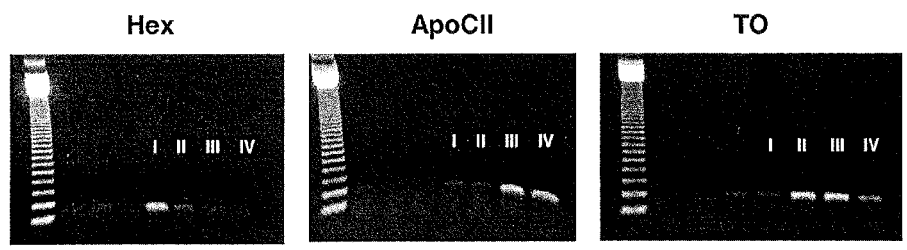
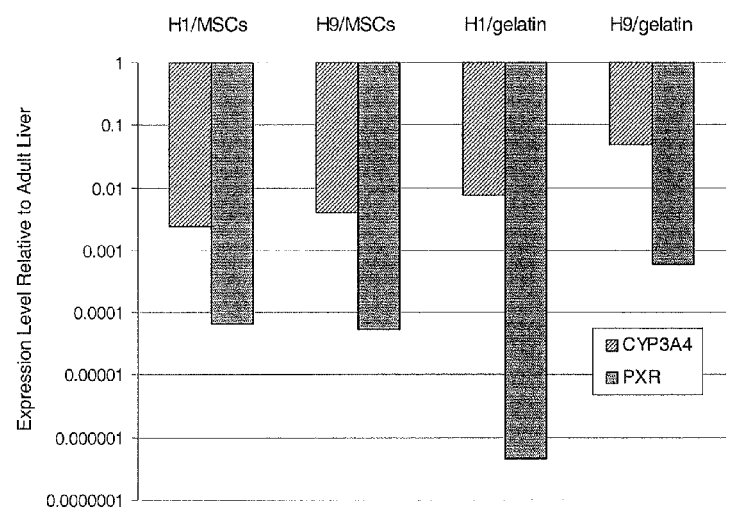

PROTOCOLS FOR MAKING HEPATOCYTES FROM EMBRYONIC STEM CELLS

REFERENCE TO RELATED APPLICATIONS

This application is a continuation of application Ser. No. 12/277,136, filed Nov. 24, 2008, which is a continuation of application Ser. No. 10/810,311, filed Mar. 26, 2004 (now U.S. Pat. No. 7,473,555), which is a continuation-in-part of application Ser. No. 10/087,142, filed Mar. 1, 2002 (now U.S. Pat. No. 7,282,366), which is a continuation-in-part of application Ser. No. 10/001,267, filed Oct. 31, 2001 (now U.S. Pat. No. 7,256,042), which is a continuation-in-part of application Ser. No. 09/872,182, filed May 31, 2001 (now U.S. Pat. No. 6,506,574), and a continuation-in-part of International Patent Application No. PCT/US01/13471, filed Apr. 26, 2001, which claims priority to Provisional Application No. 60/200,095, filed Apr. 27, 2000. All of the above-listed applications and patents are hereby incorporated herein by reference in their entirety.

This application does not claim priority to related U.S. utility application Ser. No. 09/718,308 (093/002), filed Nov. 20, 2000 (now U.S. Pat. No. 6,458,589), for which U.S. Ser. No. 60/200,095 is also a priority document. However, U.S. Pat. No. 6,458,589, and International Patent Publications WO 01/51616 (091/200pct) and WO 03/020920 (091/300pct), along with the priority documents listed in the preceding paragraph, are hereby incorporated herein by reference in their entirety with respect to supporting information related to the features, culturing, and use of undifferentiated stem cells and hepatocyte lineage cells as claimed in the present application.

TECHNICAL FIELD

This invention relates generally to the field of cell biology of embryonic cells and liver cells. The disclosure provides new approaches to directed differentiation of human pluripotent stem cells into cells bearing features and important enzymatic functions of hepatocytes.

BACKGROUND

Cost-effective development of new pharmaceutical agents depends closely on the ability to prescreen drug candidates in high throughput cellular based assays. The compounds are tested not only for their ability to induce the desired effect on the target tissue, but also for a low side-effect profile in unrelated metabolic systems.

Since the liver controls the clearance and metabolism of most small-molecule drugs, a cornerstone of the screening process is to evaluate the effect on liver cells. One objective is to determine whether the compounds or their metabolites have any potential for hepatotoxicity—measured by an effect of the compound on cell viability, morphology, phenotype, or release of metabolites and enzymes that correlate with a compromise in cell function. Another objective is to evaluate the profile of metabolites produced from the compound, since the metabolites may have collateral effects on other cell types.

For this reason, there is a high commercial demand for high quality hepatocytes by the pharmaceutical industry. Tumor cell lines and cells from non-human mammals are often unsuitable for this process, and so pharmaceutical companies are often forced to use clinical samples and primary cultures of human cells. Because of supply and consistency issues, there is a strong need to identify a source that could provide large quantities of human hepatocytes having standardized and reproducible criteria of quality.

Unfortunately, culture systems for expanding human hepatocytes have been difficult to develop. European Patent Application EP 953 633 A1 proposes a cell culturing method and medium for producing proliferated and differentiated human liver cells, apparently from donated human liver tissue. In most people's hands, the replication capacity of human hepatocytes in culture has been disappointing. As a remedy, it has been proposed that hepatocytes be immortalized by transfecting with large T antigen of the SV40 virus (U.S. Pat. No. 5,869,243). Alternatively, it has been proposed that a line of hepatocytes be developed that has had its replicative capacity increased using telomerase reverse transcriptase (WO 02/48319).

Geron Corporation has been working on a different model to supply hepatocytes to the pharmaceutical industry. Pluripotent stem cells (exemplified by embryonic stem cells) can be grown almost indefinitely in culture, providing a virtually limitless supply of uniform source material. Thomson et al. (U.S. Pat. No. 5,843,780; Proc. Natl. Acad. Sci. USA 92:7844, 1995) were the first to successfully culture human embryonic stem (hES) cells (Science 282:114, 1998). These cells are capable of ongoing proliferation in vitro without differentiating, they retain a normal karyotype, and they retain the capacity to differentiate to produce all adult cell types. However, if allowed to differentiate in vitro, hES cells form a heterogeneous mixture of phenotypes, representing a spectrum of different cell lineages.

This disclosure shows how hES cells can be directed to differentiate into cells of the hepatocyte lineage en masse, generating high quality cell populations with reproducible standards. This will provide the pharmaceutical industry with a reliable and scalable source of human hepatocytes that have standardized characteristics. The technology will allow the hepatic toxicity and metabolic profile of new drugs to be determined in vitro, before initiation of human clinical trials. It will also set the stage for development of the hepatocytes themselves as therapeutic compositions to supplement liver function in patients affected by hepatic failure.

SUMMARY

The procedures described in this disclosure are used for making hepatocyte lineage cells from precursor cells, such as undifferentiated cells of embryonic origin. Embodiments of the invention include cells produced by the derivation system, their equivalents, and methods for making and using them for research and commercial purposes.

Some embodiments of the differentiation process can be portrayed on a framework that involves culturing undifferentiated primate pluripotent stem cells in a manner (or with a means for) causing differentiation into cells having characteristics of fetal endoderm; then culturing the cells in a manner (or with a means for) causing differentiation into cells having characteristics of hepatocyte progenitor cells; and then culturing the cells in a manner (or with a means for) causing differentiation into mature hepatocytes.

Markers for identifying intermediate and mature cells obtained in this process are listed later on in this disclosure. For example, early progenitors may express Hex, Sox17, HNF-3a, HNF-3b, or α-fetoprotein; hepatocyte progenitors may express γ-glutamyl tranpeptidase, HNF-4a isomer a7/a8, albumin, $\alpha_1$-antitrypsin (AAT), or Matripase 2; and mature hepatocytes may express ApoCII, tyrosine oxygenase, CYP3A4, CYP3A7, HNF-4a isomer a1/a2, and LST-1. Mature cells are also typically positive for $\alpha_1$-antitrypsin, albumin, asialoglycoprotein receptor, glycogen storage, p450 enzyme activity (such as CYP3A4), glucose-6-phosphatase activity, negative for less mature markers such as $\alpha$-fetoprotein, and have the morphological features of adult hepatocytes.

When the differentiation process is done in a step-wise fashion, an early step may involve forming embryoid bodies, or culturing with non-specific or early acting agents such as DMSO, fibroblast growth factors such as FGF-8, or bone morphogenic proteins such as BMP-2, 4, and 7. An intermediate step may involve culturing with a histone deacetylase inhibitor such as butyrate, or with a bone morphogenic protein, a growth factor like EGF, a corticosteroid like dernethasone, or Oncostatin M. A later step may involve culturing with a hepatocyte growth factor, either alone, or with other growth factors in conjunction with agents that help with end-stage maturation. Of course, each of these three steps can be subdivided, preceded, or followed by additional manipulations or culture environments, so that the total number of steps in the differentiation pathway comprises four, five, or more than five discrete steps. Other agents and combinations that promote cell differentiation according to this invention are illustrated in the sections that follow.

This invention also embodies cells made according to these protocols, and cell combinations useful in making or utilizing the derived cells. In one such embodiment, the endodermal cells, hepatocyte precursors, or mature hepatocyte-like cells of this invention are part of a system which also comprises the stem cells from which they were derived, or one or more other cell types obtained along the differentiation pathway. Another embodiment is hepatocyte lineage cells at about the same stage of differentiation, obtained from the same parental line, but genetically engineered to express useful allotypic differences such as variations in the cytochrome p450 enzyme system.

Also embodied in this invention is the use of cells produced according to this invention for the purposes of drug screening, or clinical therapy. Drug screening is performed by combining the cells with a substance to be screened, and then determining if the substance is toxic or changes the cell phenotype. Clinical therapy can be conducted by formulating the hepatocyte-lineage cells in a medicament for administration to the subject, or by loading the cells in a mechanical device with which the subject is treated ex vivo.

These and other embodiments of the invention are described in the sections that follow.

DRAWINGS

FIG. 1 provides a scheme for making hepatocyte lineage cells from human embryonic stem cells (hES), by sequentially culturing in four different media formulations. This scheme makes sequential use of DMSO, sodium n-butyrate (NaBut) and growth factors (GF) in a particular hepatocyte culture medium (HCM). The hepatocytes obtained have the cuboidal shape and large nucleus characteristic of adult hepatocytes (middle panel). They also express characteristic markers (albumin, $\alpha_1$-antitrypsin (AAT), CK18, are glycogen positive, and are $\alpha$-fetoprotein (AFP) negative) (bottom panel).

FIG. 2 provides another scheme for making hepatocyte lineage cells, exemplified in Example 5 of this disclosure. Butyrate is omitted. Instead, differentiation is started using DMSO, and then matured with a combination of growth factors (epidermal growth factor, EGF; hepatocyte growth factor, HGF), a glucocorticoid (dexamethasone, Dex), and Oncostatin M (OSM). The culture was further matured by culturing with HGF, producing cells having morphological features of hepatocytes (middle panel). The bottom panel shows expression of various cell markers as detected by RT-PCR (real-time PCR amplification of mRNA), through the various stages of the differentiation protocol.

FIG. 3 provides two more schemes for making hepatocyte lineage cells, exemplified in Examples 6 and 7. The Growth Factor Protocol involves predifferentiating the cells with DMSO in the presence of fibroblast growth factor, and then maturing the cells with Oncostatin M and HGF. The Endoderm Protocol involves predifferentiating the cells with bone morphogenic proteins (BMPs), then maturing the hepatocytes first with Oncostatin M, then with HGF. The bottom panel shows the morphological change in the cells at various stages in the process.

FIG. 4 is a working guide illustrating some useful markers for various stages of differentiation, discussed later in the disclosure.

FIG. 5 shows the marker expression in hepatocytes obtained according to the Endoderm Protocol. The top panel shows expression of Hex (an early marker) by Stage I cells, and ApoCII and tyrosine oxidase (TO) (both late markers) by Stage III and IV cells, as detected on Western blots. The bottom panel shows expression of CYP3A4 and the regulator PXR as detected by RT-PCR.

FIG. 6 is a set of $A_{242}$ tracings of an HPLC assay for CYP3A4 enzyme activity in hepatocytes obtained according to the Endoderm Protocol. Cells pretreated with the CYP3A4 inducer rifampicin, and then administered the substrate testosterone, produce the product $\beta$-hydroxy testosterone (A). Absence of the substrate (C), or presence of the inhibitor ketoconozole (B) blocks $\beta$-OH testosterone production. Panel (D) shows an expanded view of the product peak formed by rifampicin induced cells; (E) is spiked with $\beta$-OH to confirm the position of the product. These data are consistent with p450 enzyme activity in the hES cell derived hepatocytes.

DETAILED DESCRIPTION

This invention provides a system for preparing differentiated cells of the hepatocyte lineage from primate pluripotent stem (pPS) cells, exemplified by human embryonic stem (hES) cells.

The preparation of hepatocytes for use in drug screening and human therapy has been a priority at Geron Corporation for many years. Previous patent disclosures in this series (U.S. Pat. Nos. 6,458,589 and 6,506,574; PCT publication WO 01/81549) demonstrated for the first time that relatively homogeneous populations of cells having a number of identifiable features of hepatocytes can be produced from hES cells, even though these cells are in no way precommitted to the hepatocyte lineage. Exemplary differentiation protocols involved the use of tyrosine hydroxylase inhibitors, or chemical analogs of n-butyrate, supplemented by other hepatocyte differentiation and maturation agents. Additional information in the present disclosure provides information and data that represents confirmation, enhancement, and new inventions made during qualification and commercial development of pPS derived hepatocytes.

A framework for many of the protocols described in this application is a step-wise approach to the differentiation process. There is first a stage in which undifferentiated pPS cells are expanded to the volume required, and optionally primed for the differentiation process. There is then a stage in which differentiation is initiated in a non-specific manner, or in a manner intended to direct the cells towards enrichment for endodermal cells (the germ layer from which the liver emerges in utero). This is followed by a stage, which is intended to bring the cells into a commitment towards the liver cell lineage, and a stage in which the cells are pushed further down the pathway towards mature hepatocytes.

This framework was designed in concert with the discovery of new protocols in which the presence of tyrosine hydroxylase inhibitors is not required. Removal of butyrate from the system is believed to have several advantages in the use of the cells for pharmaceutical drug screening and clinical use. Different options for particular agents at each stage of the process validate the general utility of the derivation system provided in this disclosure.

As shown in FIGS. 1, 2, and 3, cell populations obtained according to this invention had hepatocyte characteristics that are desirable in cells used for commercial purposes: relatively uniform in appearance and marker expression, a polygonal phenotype, and markers characteristic of adult hepatocytes. FIG. 6 supports the idea that select hepatocyte lineage cells of this invention express the cytochrome p450 enzyme CYP3A4, which is particularly desirable for cells used in general drug screening.

What follows is a further description of particular embodiments of the culture system of this invention, and how it can be used to generate hepatocyte lineage cells from pluripotent embryonic stem cells of primate origin. Since pluripotent stem cells can proliferate in culture for over 300 population doublings, the invention described in this disclosure provides an almost limitless supply of hepatocyte-like cells, suitable for a variety of commercial and research purposes.

DEFINITIONS

In the context of cell ontogeny, a "differentiated cell" is a cell that has progressed further down the developmental pathway than the cell it is being compared with. Thus, pluripotent embryonic stem cells can differentiate to lineage-restricted precursor cells, such as endoderm cells, and then to hepatocyte precursors and mature cells.

When differentiated cells obtained from pluripotent stem cells are referred to by a tissue type (such as endoderm cells or hepatocytes), the name is provided mostly for convenience, and without implying any limitation not otherwise required. Typically, the pPS derived cells will have many morphological or phenotypic characteristics of the cell type referred to, and a paucity of features not usually found in such cells. It is recognized, however, that ontogeny in a culture vessel differs from ontogeny in utero, and that this may have an impact on particular characteristics. This does not affect the making or using of the cells of the invention where the characteristics explicitly required are present.

A "hepatocyte precursor cell" or a "hepatocyte stem cell" refers to a cell that can proliferate and further differentiate into a hepatocyte, under suitable environmental conditions. Such cells may on occasion have the capacity to produce other types of progeny, such as oval cells, bile duct epithelial cells, or additional hepatocyte precursor cells. A "hepatocyte lineage cell" is any cell which is not pluripotent, and found somewhere on the ontology of hepatocytes (from endoderm down to mature cells).

A hepatocyte differentiation or maturation agent of this disclosure is a member of a collection of compounds that can be used in preparing and maintaining the differentiated cells of this invention. These agents are further described and exemplified in the sections that follow. In this particular disclosure, the terms are not meant to imply a particular mode or timing of action, and no such limitation should be inferred.

Prototype "primate Pluripotent Stem cells" (pPS cells) are pluripotent cells derived from pre-embryonic, embryonic, or fetal tissue at any time after fertilization. They have the characteristic of being capable under appropriate conditions of producing progeny of several different cell types that are derivatives of all of the three germinal layers (endoderm, mesoderm, and ectoderm), according to a standard art-accepted test, such as the ability to form a teratoma in 8-12 week old SCID mice. Included in the definition of pPS cells are embryonic cells of various types, exemplified by human embryonic stem (hES) cells, and human embryonic germ (hEG) cells. The pPS cells are preferably not derived from a malignant source. It is desirable (but not always necessary) that the cells be euploid. Depending on their source and method of culture, the pPS cells may or may not be totipotent, in the sense that they have the capacity of developing into all the different cell types of the human body.

pPS cell cultures are described as "undifferentiated" when a substantial proportion of stem cells and their derivatives in the population display morphological characteristics of undifferentiated cells, distinguishing them from differentiated cells of embryo or adult origin. It is understood that colonies of undifferentiated cells within the population will often be surrounded by neighboring cells that are differentiated.

"Feeder cells" or "feeders" are terms used to describe cells of one type that are co-cultured with cells of another type, to provide an environment in which the cells of the second type can grow. pPS cell populations are said to be "essentially free" of feeder cells if the cells have been grown through at least one round after splitting in which fresh feeder cells are not added to support the growth of pPS cells.

The term "embryoid bodies" refers to heterogeneous aggregates of differentiated cells that appear when pPS cells overgrow in monolayer cultures, or are maintained in suspension cultures. Embryoid bodies are a mixture of different cell types, typically from several germ layers, distinguishable by morphological criteria and cell markers detectable by immunocytochemistry.

A "growth environment" is a culture environment in which cells of interest will proliferate, differentiate, or mature in vitro. Features of the environment include the medium in which the cells are cultured, any growth factors or differentiation-inducing factors, and a supporting structure (such as a substrate or solid surface) if present.

General Techniques

General methods in molecular genetics and genetic engineering are described in the current editions of *Molecular Cloning: A Laboratory Manual*, (Sambrook et al., Cold Spring Harbor); *Gene Transfer Vectors for Mammalian Cells* (Miller & Calos eds.); and *Current Protocols in Molecular Biology* (F. M. Ausubel et al. eds., Wiley & Sons). Cell biology, protein chemistry, and antibody techniques can be found in *Current Protocols in Protein Science* (J. E. Colligan et al. eds., Wiley & Sons); *Current Protocols in Cell Biology* (J. S. Bonifacino et al., Wiley & Sons) and *Current protocols in Immunology* (J. E. Colligan et al. eds., Wiley & Sons.). Reagents, cloning vectors, and kits for genetic manipulation referred to in this disclosure are available from commercial vendors such as BioRad, Stratagene, Invitrogen, ClonTech, and Sigma-Aldrich Co.

Cell culture methods are described generally in the current edition of *Culture of Animal Cells: A Manual of Basic Technique* (R. I. Freshney ed., Wiley & Sons); *General Techniques of Cell Culture* (M. A. Harrison & I. F. Rae, Cambridge Univ. Press), and *Embryonic Stem Cells: Methods and Protocols* (K. Turksen ed., Humana Press). Tissue culture supplies and reagents are available from commercial vendors such as Gibco/BRL, Nalgene-Nunc International, Sigma Chemical Co., and ICN Biomedicals.

Specialized reference books relevant to this disclosure include *The Hepatocyte Review*, M. N. Berry & A. M. Edwards Eds., Kluwer Academic Publishers, 2000; *Hepatocyte Transplantation* (*Falk Symposium*, 126), S. Gupta, J. Klempnauer, P. L. M. Jansen, M. P. Manns Eds., Kluwer Academic Publishers, 2002; *Handbook of Drug Screening*, R. Seethala & P. B. Fernandes Eds., Marcel Dekker, 2001; *Bioassay Techniques for Drug Development*, Atta-Ur-Rahman, M. I. Choudhary, W. J. Thomsen, A. Rahman, Taylor & Francis, 2001.

Sources of Stem Cells

This invention can be practiced using stem cells of various types. Particularly suitable for use in this invention are primate pluripotent stem (pPS) cells derived from tissue formed after gestation, such as a blastocyst, or fetal or embryonic tissue taken any time during gestation. Non-limiting examples are primary cultures or established lines of embryonic stem cells or embryonic germ cells, as described below. The techniques of this invention can also be implemented directly with primary embryonic or fetal tissue, deriving differentiated cells directly from primary embryonic cells without first establishing an undifferentiated cell line.

The illustrations provided in the Example section ensue from work done with human embryonic stem cells. However, except where otherwise specified, the invention can be practiced using stem cells of any vertebrate species. Included are pluripotent stem cells from humans; as well as non-human primates, and other non-human mammals.

Embryonic Stem Cells

Embryonic stem cells can be isolated from primate tissue (U.S. Pat. No. 5,843,780; Thomson et al., Proc. Natl. Acad. Sci. USA 92:7844, 1995). Human embryonic stem (hES) cells can be prepared from human blastomeres using techniques described by Thomson et al. (U.S. Pat. No. 6,200,806; Science 282:1145, 1998; Curr. Top. Dev. Biol. 38:133 ff., 1998) and Reubinoff et al. (Nature Biotech. 18:399, 2000). Equivalent cell types to hES cells include their pluripotent derivatives, such as primitive ectoderm-like (EPL) cells, as outlined in WO 01/51610 (Bresagen).

In one method, the zona pellucida is removed from developed blastocysts by brief exposure to pronase (Sigma). The inner cell masses are isolated by immunosurgery, in which blastocysts are exposed to a 1:50 dilution of rabbit anti-human spleen cell antiserum for 30 min, then washed three times for 5 min in DMEM, and exposed to a 1:5 dilution of Guinea pig complement (Gibco) for 3 min (Solter et al., Proc. Natl. Acad. Sci. USA 72:5099, 1975). After two further washes in DMEM, lysed trophectoderm cells are removed from the intact inner cell mass (ICM) by gentle pipetting, and the ICM cells are plated on mEF feeder layers.

After 9 to 15 days, inner cell mass-derived outgrowths are dissociated into clumps, either by exposure to calcium and magnesium-free phosphate-buffered saline (PBS) with 1 mM EDTA, by exposure to dispase or trypsin, or by mechanical dissociation with a micropipette; and then replated on mEF in fresh medium. Growing colonies having undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1-2 weeks by brief trypsinization, exposure to Dulbecco's PBS (containing 2 mM EDTA), exposure to type IV collagenase (~200 U/mL; Gibco), or by selection of individual colonies by micropipette. Clump sizes of about 50 to 100 cells are optimal.

Embryonic Germ Cells

Human Embryonic Germ (hEG) cells can be prepared from primordial germ cells as described in Shamblott et al., Proc. Natl. Acad. Sci. USA 95:13726, 1998 and U.S. Pat. No. 6,090,622.

Briefly, genital ridges taken after ~8-11 weeks are rinsed with isotonic buffer, then placed into 0.1 mL 0.05% trypsin/ 0.53 mM sodium EDTA solution (BRL) and cut into <1 mm$^3$ chunks. After disaggregation, the cells are incubated 1 h or overnight at 37° C. in ~3.5 mL EG growth medium (DMEM containing D-glucose, NaHCO$_3$; 15% ES qualified fetal calf serum; 2 mM glutamine; 1 mM sodium pyruvate; 1000-2000 U/mL human recombinant leukemia inhibitory factor; 1-2 ng/mL human recombinant bFGF; and 10 μM forskolin (in 10% DMSO).

The cells are then resuspended in 1-3 mL of EG growth medium, and plated onto a feeder layer (e.g., STO cells, ATCC No. CRL 1503, inactivated with 5000 rad γ-irradiation). The first passage is done after 7-10 days, and then cultured with daily replacement of medium until cell morphology consistent with EG cells is observed, typically after 7-30 days or 1-4 passages.

Other Stem Cells

By no means does the practice of this invention require that a human embryo or blastocyst be disaggregated in order to produce the pPS or embryonic stem cells useful as the starting material for making the differentiated cells of this invention. hES cells can be obtained from established lines obtainable from public depositories (for example, the WiCell Research Institute, Madison Wis. U.S.A., or the American Type Culture Collection, Manassas Va., U.S.A.). U.S. Patent Publication 2003-0113910 A1 reports pluripotent stem cells derived without the use of embryos or fetal tissue. It may also be possible to reprogram cord blood or other progenitor cells into pPS cells by using a factor that induces the pluripotent phenotype (Chambers et al., Cell 113:643, 2003; Mitsui et al., Cell 113:631, 2003). Under appropriate conditions, any cell that otherwise meets the definitions for pPS or hES cells can be used for the derivation of differentiated cells.

The techniques provided in this disclosure can also be used to maintain or advance the differentiation of pluripotent stem cells (such as embryonic cells) from mammals and other species different from primates. Exemplary references include the article by G. R. Martin in Proc. Natl. Acad. Sci. USA 78:7634-8, 1981, and the texts *Embryonic Stem Cells: Methods and Protocols*, K. Turksen, Humana Press, 2001; and *Stem Cell Biology*, D. Marshak, R. Gardner, D. Gottlieb Eds., Cold Spring Harbor Laboratory, 2002.

Propagation of pPS Cells in an Undifferentiated State pPS cells can be propagated continuously in culture, using culture conditions that promote proliferation without promoting differentiation. Exemplary serum-containing ES medium is made with 80% DMEM (such as Knockout DMEM, Gibco), 20% of either defined fetal bovine serum (FBS, Hyclone) or serum replacement (WO 98/30679), 1% non-essential amino acids, 1 mM L-glutamine, and 0.1 mM β-mercaptoethanol. Just before use, human bFGF is added to 4 ng/mL (WO 99/20741, Geron Corp.).

The pPS cells can be expanded in the undifferentiated state only by culturing in an environment that inhibits differentiation. Traditionally, pPS cells are cultured on a layer of feeder cells derived from embryonic or fetal tissue of the mouse. Culture plates are plated with 375,000 irradiated mEFs per well, irradiated to inhibit proliferation but permit synthesis of factors that support pPS cells, and used 5 h to 4 days after plating (U.S. Pat. No. 6,200,806). Human feeder cells have recently been developed that support proliferation of human embryonic stem cells without differentiation (WO 01/51616; U.S. Ser. No. 09/888,309; Geron Corp.). The cells are obtained by differentiating hES cells, selecting cells that have the desired activity, and then immortalizing them by transfecting them to express telomerase reverse transcriptase.

pPS cells can be maintained in an undifferentiated state even without feeder cells. The environment for feeder-free cultures includes a suitable culture substrate, particularly an extracellular matrix such as Matrigel® or laminin. The pPS cells are plated at >15,000 cells $cm^{-2}$ (optimally 90,000 $cm^{-2}$ to 170,000 $cm^{-2}$). Feeder-free cultures are supported by a nutrient medium containing factors that support proliferation of the cells without differentiation.

Such factors may be introduced into the medium by culturing the medium with cells secreting such factors, such as irradiated (4,000 rad) primary mouse embryonic fibroblasts, telomerized mouse fibroblasts, or human feeder cells derived from pPS cells. Medium can be conditioned by plating the feeders at a density of ~5-6×10⁴ $cm^{-2}$ in a serum free medium such as KO DMEM supplemented with 20% serum replacement and 4 to 8 ng/mL bFGF. Medium that has been conditioned for 1-2 days is supplemented with more bFGF, and used to support pPS cell culture for 1-2 days (see WO 99/20741; WO 01/51616; and Xu et al., Nat. Biotechnol. 19:971, 2001). Alternatively, medium can be produced to support feeder-free growth without conditioning, by adding agents such as bFGF, forskolin, and stem cell factor (WO 99/20741; WO 03/020920). Exemplary is X-VIVO™ 10 (Biowhittaker) or QBSF™-60 medium (Quality Biological Inc.), containing 40 ng/mL added bFGF, and optionally 15 ng/mL Stem Cell Factor or 75 ng/mL Flt-3 ligand.

Under the microscope, ES cells appear with high nuclear/cytoplasmic ratios, prominent nucleoli, and compact colony formation with cell junctions that are difficult to discern. Primate ES cells typically express stage-specific embryonic antigens (SSEA) 3 and 4, markers detectable using antibodies designated Tra-1-60 and Tra-1-81 (Thomson et al., Science 282:1145, 1998), and telomerase activity. Differentiation of pPS cells in vitro results in the loss of SSEA-4, Tra-1-60, and Tra-1-81 expression, and increased expression of SSEA-1, which is also found on undifferentiated hEG cells.

Materials and Procedures for Differentiating pPS Cells

Differentiated cells of this invention can be made by culturing pPS cells in one or more culture environments under conditions that promote the desired extent of differentiation. The environments may each contain one or more hepatocyte differentiation and maturation agents. The resulting cells have characteristics of hepatocyte lineage cells of progressive maturity.

Some of the protocols exemplified in this disclosure can be thought of as following a framework in which the cells are taken through different stages of maturity on their way towards becoming mature hepatocytes. Conceptually, the steps follow the pathway from undifferentiated stem cells, through early germinal tissue (endodermal cells), to early-stage hepatic progenitors (committed to make hepatocytes and perhaps other types of liver cells), and then perhaps through other discernable intermediate stages, leading ultimately to relatively mature hepatocyte-like cells.

In some embodiments, the framework is implemented by changing the medium in which the cells are cultured for each of the stages. This framework is presented as a convenient way for the reader to think about the differentiation process, and is not intended to be limiting. Unless expressly indicated otherwise, it may be possible for multiple stages to be completed in the same medium, or for steps to be combined or placed in a different order. Designation of the phenotypic outcome of each step is also not required to implement the invention, except where specific markers are indicated, in which case the outcome is satisfied upon expression of the markers as required. Designation of each "Stage" in particular protocols may not correspond in maturity to stages in other protocols. Titles such as *Growth Factor Protocol and Endoderm Protocol* are monikers only, and do not imply any limitations to the claimed invention.

Suitable Differentiation and Maturation Factors

Part of the growth environment influencing differentiation is the medium in which the cells are cultured. At several stages in the process, differentiation is enhanced by including in the medium certain substances (referred to as differentiation or maturation factors or agents). While not implying any limitation on the practice of the invention, it is hypothesized that the factors either help induce cells to commit to a more mature phenotype—or preferentially promote survival of the mature cells—or have a combination of both these effects.

A prototype hepatocyte differentiation and maturation factor is n-butyrate, as described in previous patent disclosures in this series (U.S. Pat. No. 6,458,589, U.S. Pat. No. 6,506,574; WO 01/81549). Homologs of n-butyrate can readily be identified that have a similar effect, and can be used as substitutes in the practice of this invention. Some homologs have similar structural and physicochemical properties to those of n-butyrate: acidic hydrocarbons comprising 3-10 carbon atoms, and a conjugate base selected from the group consisting of a carboxylate, a sulfonate, a phosphonate, and other proton donors. Examples include isobutyric acid, butenoic acid, propanoic acid, other short-chain fatty acids, and dimethylbutyrate. Also included are isoteric hydrocarbon sulfonates or phosphonates, such as propanesulfonic acid and propanephosphonic acid, and conjugates such as amides, saccharides, piperazine and cyclic derivatives. A further class of butyrate homologs is inhibitors of histone deacetylase. Non-limiting examples include trichostatin A, 5-azacytidine, trapoxin A, oxamflatin, FR901228, cisplatin, and MS-27-275.

Another class of factors is organic solvents like DMSO. Alternatives with similar properties include but are not limited to dimethylacetamide (DMA), hexmethylene bisacetamide, and other polymethylene bisacetamides. Solvents in this class are related, in part, by the property of increasing membrane permeability of cells. Also of interest are solutes such as nicotinamide.

Other hepatocyte differentiation and maturation factors illustrated in this disclosure include soluble growth factors (peptide hormones, cytokines, ligand-receptor complexes, and other compounds) that are capable of promoting the growth of cells of the hepatocyte lineage. Such factors include but are not limited to epidermal growth factor (EGF), insulin, TGF-α, TGF-β, fibroblast growth factor (FGF), heparin, hepatocyte growth factor (HGF), Oncostatin M (OSM), IL-1, IL-6, insulin-like growth factors I and II (IGF-I, IGF-2), heparin binding growth factor 1 (HBGF-1), and glucagon. The skilled reader will already appreciate that Oncostatin M is structurally related to Leukemia inhibitory factor (LIF), Interleukin-6 (IL-6), and ciliary neurotrophic factor (CNTF).

Another class of factors is corticosteroids, particularly glucocorticoids. Each is a steroid or steroid mimetic that affects intermediary metabolism, especially promoting hepatic glycogen deposition, and inhibiting inflammation. Included are naturally occurring hormones exemplified by cortisol, synthetic glucocorticoids such as dexamethazone (U.S. Pat. No. 3,007,923) and its derivatives, prednisone, methylprednisone, hydrocortisone, and triamcinolone (U.S. Pat. No. 2,789,118) and its derivatives.

The ability of a particular compound or combination of compounds to act as hepatocyte differentiation or maturation factors can be tested according to the culturing and assessment protocols provided in this disclosure. Efficacy of particular test compounds or combinations of compounds can be assessed by their effect on cell morphology, marker expression, enzymatic activity, proliferative capacity, or other features of interest, which is then determined in comparison with parallel cultures that did not include the candidate compound.

Most of the protein factors listed in this disclosure are available in the form that naturally occurs in humans, or a functional fragment thereof. Besides human proteins, species orthologs (particularly mouse, bovine, and other mammals) usually work equally well. The skilled reader will also recognize that most of the factors listed in this section will have direct equivalents that can be substituted into the process without departing from the essence of the invention. For example, natural or artificial protein homologs or functionally related molecules that bind to the same receptor can be used as a comparable substitute. Antibodies and antibody fragments that bind the receptor so as to activate it in a similar way can also be used. Also equivalent are biochemical agents or small molecule compounds that have the effect of activating the same intracellular pathways as the prototype ligand.

Designing a Differentiation Protocol

Some growth conditions described in this application can accomplish a good deal of the differentiation process on their own. There are often advantages in pursuing a multi-step process towards the making of hepatocyte-like cells. Such advantages include ease of scale-up, qualification, and uniformity, and enhancement of certain characteristics that the user may find desirable.

Early stage differentiation from pluripotent stem cells can be accomplished in a non-specific or directed fashion. In some occasions, differentiation of the pPS is initiated by first forming embryoid bodies or cell clusters (Example 1). Other agents suitable for initiating the differentiation process include DMSO or retinoic acid (Example 3), and similar compounds listed in the preceding section. Differentiation can also be initiated by culturing with biological factors that push cells towards a more active phenotype having functional activity of endoderm cells. Exemplary is the family of bone morphogenic proteins, such as BMP-2, BMP-4, and BMP-7 (Example 7). The presence of growth factors (such as those in the FGF family) may be useful adjuncts during the early differentiation stage (Example 6), or may be used to prime the undifferentiated cells before differentiation is initiated (Example 7).

Once differentiation has been initiated, progress along the differentiation pathway can be promoted or enhanced by factors such as butyrate (or a structural or functional analog) (Example 3), or by a suitable mixture of biological factors. Exemplary are Oncostatin M (or a similar protein listed in the previous section), bone morphogenic proteins (Example 3), optionally in the presence of a corticosteroid like dexamethasone, or one or more growth factors, such as FGF, EGF (Example 5), nerve growth factor (Example 7), insulin (Example 3), glucagon (Example 3), or one of the growth factors listed in the previous section. It may be of assistance to design factor combinations in the early and middle stages of differentiation based on the natural environment of the prospective liver in utero, as influenced by factors provided by the ventral foregut endoderm, the prospective ventral pancreas, and the septum transversum mesenchyme.

Where desired, further maturation of the culture can be accomplished by a refinement of the factors present in the culture medium. Hepatocyte growth factor (HCM, a Scatter Factor), and other ligands that activate the c-Met receptor, are useable at any stage in this process, but they are especially helpful towards later stages of maturation. Other growth factors, optionally used in conjunction with corticosteroids or growth factors, may have a similar effect.

Differentiation down the hepatocyte lineage can be assisted by using a different base medium from what is required for culture of the undifferentiated cells, formation of embryoid bodies, or early stage differentiation. Suitable media such as some optimized for hepatocyte culture are available commercially, such as "Hepatocyte Culture Medium" by Clonetics (Example 3). Other formulations are described in U.S. Pat. No. 5,030,105, U.S. Pat. No. 5,576,207; EP 953,633; Angelli et al., Histochem. J. 29:205, 1997; and Gomez-Lechon et al., p. 130 ff. in *In vivo Methods in Pharmaceutical Research*, Academic Press, 1997. The differentiating cells can also be plated onto a suitable substrate, such as irradiated feeder cells (Example 7), or an extracellular matrix components like Matrigel® (Example 1) or gelatin (Example 7).

Once cells of the desired phenotype are obtained, the cell population can be harvested for any desired use. In certain differentiated cell populations of this invention, the cells are sufficiently uniform in phenotype that they can be harvested simply by releasing the cells from the substrate (e.g., using collagenase, trypsin, or by physical manipulation), and optionally washing the cells free of debris. If desired, the harvested cells can be further processed by positive selection for desired features, or negative selection for undesired features. For example, cells expressing surface markers or receptors can be positively or negatively selected by incubating the population with an antibody or conjugate ligand, and then separating out the bound cells—either by labeled sorting techniques, adsorption to a solid surface, or complement-mediated lysis of the undesired phenotype.

Harvested cells can be transferred into other culture environments for further propagation, or prepared for drug screening or pharmaceutical formulation as described below.

Characteristics of Differentiated Cells

Cells can be characterized according to a number of phenotypic criteria. The criteria include but are not limited to the detection or quantitation of expressed cell markers, enzymatic activity, and the characterization of morphological features and intercellular signaling.

Certain differentiated pPS cells embodied in this invention have morphological features characteristic of hepatocytes. The features are readily appreciated by those skilled in evaluating such things, and include any or all of the following: a polygonal cell shape, a binucleate phenotype, the presence of rough endoplasmic reticulum for synthesis of secreted protein, the presence of Golgi-endoplasmic reticulum lysosome complex for intracellular protein sorting, the presence of peroxisomes and glycogen granules, relatively abundant mitochondria, and the ability to form tight intercellular junctions resulting in creation of bile canalicular spaces. A number of these features present in a single cell are consistent with the cell being a member of the hepatocyte lineage. Unbiased determination of whether cells have morphologic features characteristic of hepatocytes can be made by coding micrographs of differentiated pPS cells, adult or fetal hepatocytes, and one or more negative control cells, such as a fibroblast, or RPE (Retinal pigment epithelial) cells—then evaluating the micrographs in a blinded fashion, and breaking the code to determine if the differentiated pPS cells are accurately identified.

Cells of this invention can also be characterized according to whether they express phenotypic markers characteristic of cells of the hepatocyte lineage. Cell markers useful in distinguishing liver progenitors, hepatocytes, and biliary epithelium, are shown in Table 1 (adapted from p 35 of Sell & Zoran, *Liver Stem Cells*, R. G. Landes Co., TX, 1997; and Grisham et al., p 242 of *Stem Cells*, Academic Press, 1997).

controls for the markers of mature hepatocytes include adult hepatocytes of the species of interest, and established hepatocyte cell lines. The reader is cautioned that permanent cell lines or long-term liver cell cultures may be metabolically altered, and fail to express certain characteristics of primary hepatocytes. Negative controls include cells of a separate lineage, such as an adult fibroblast cell line, or retinal pigment epithelial (RPE) cells. Undifferentiated pPS cells are positive for some of the markers listed above, but negative for markers of mature hepatocytes, as illustrated in the examples below.

Tissue-specific protein and oligosaccharide determinants listed in this disclosure can be detected using any suitable immunological technique—such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Expression of an antigen by a cell is said to be "antibody-detectable" if a significantly detectable amount of antibody will bind to the antigen in a standard immunocytochemistry or flow cytom-

TABLE 1

Liver Cell Markers

| | early progenitors | hepatocytes | biliary epithelium | | early progenitors | hepatocytes | biliary epithelium |
|---|---|---|---|---|---|---|---|
| albumin | + | + | − | OC.1 | − | − | + |
| α$_1$-antitrypsin | + | + | − | OC.2 | + | − | + |
| α-fetoprotein | + | fetal & postnatal | − | OC.3 | + | − | + |
| CEA | − | − | + (?) | BD.1 | + | − | + |
| γ-glutamyl tranpeptidase | + | fetal | + | A6 | + | − | + |
| GST-P | + | fetal | + | HBD.1 | + | + | + |
| glucose-6-phosphatase | + | + | − | H.2 | − | + | − |
| catalase | − | + | − | H.4 | − | + | − |
| M2-PK | + | fetal | + | H-4 | ? | + | − |
| L-PK | − | + | fetal | H-6 | − | + | − |
| p450 mono-oxygenase | + | + | − | HES$_6$ | − | + | − |
| p-glycoprotein | ? | canaliculi | − | RL16/79 | − | postnatal | − |
| CK7 | − | − | + | RL23/36 | − | + | − |
| CK8 | + | + | + | BPC$_5$ | + | − | − |
| CK14 | + | − | − | Vimentin | − | − | fetal |
| CK18 | + | + | + | HepPar1 | + | + | − |
| CK19 | − (+) | − | + | Cell-CAM 105 | + | + | − |
| CKX | + | − | + | DPP IV | + | canaliculi | + |
| BDS$_7$ | + | − | + | lectin binding sites | + | − | + |
| OV1 | + | − | + | blood group antigens | + | − | + |
| OV6 | − | − | + | | | | |

It has been reported that hepatocyte differentiation requires the transcription factor HNF-4a (Li et al., Genes Dev. 14:464, 2000). Markers independent of HNF-4a expression include α1-antitrypsin, α-fetoprotein, apoE, glucokinase, insulin growth factors 1 and 2, IGF-1 receptor, insulin receptor, and leptin. Markers dependent on HNF-4a expression include albumin, apoAI, apoAII, apoB, apoCIII, apoCII, aldolase B, phenylalanine hydroxylase, L-type fatty acid binding protein, transferrin, retinol binding protein, and erythropoietin (EPO). Other markers of interest include those presented in the Examples and in FIG. 4.

Assessment of the level of expression of such markers can be determined in comparison with other cells. Positive etry assay, optionally after fixation of the cells, and optionally using a labeled secondary antibody or other conjugate (such as a biotin-avidin conjugate) to amplify labeling.

The expression of tissue-specific markers can also be detected at the mRNA level by Northern blot analysis, dot-blot hybridization analysis, or by real time polymerase chain reaction (RT-PCR) using sequence-specific primers in standard amplification methods (U.S. Pat. No. 5,843,780). Sequence data for the particular markers listed in this disclosure can be obtained from public databases such as GenBank. Expression at the mRNA level is said to be "detectable" according to one of the assays described in this disclosure if the performance of the assay on cell samples according to standard procedures in a typical controlled experiment results in clearly discernable hybridization or amplification product within a standard time window.

Unless otherwise required, expression of a particular marker is indicated if the corresponding mRNA is detectable by RT-PCR. Expression of tissue-specific markers as detected at the protein or mRNA level is considered positive if the level is at least 2-fold, and preferably more than 10- or 50-fold above that of a control cell, such as an undifferentiated pPS cell, a fibroblast, or other unrelated cell type.

Cells can also be characterized according to whether they display enzymatic activity that is characteristic of cells of the hepatocyte lineage. For example, assays for glucose-6-phosphatase activity are described by Bublitz (Mol Cell Biochem. 108:141, 1991); Yasmineh et al. (Clin. Biochem. 25:109, 1992); and Ockerman (Clin. Chim. Acta 17:201, 1968). Assays for alkaline phosphatase (ALP) and 5-nucleotidase (5'-Nase) in liver cells are described by Shiojiri (J. Embryol. Exp. Morph. 62:139, 1981). A number of laboratories that serve the research and health care sectors provide assays for liver enzymes as a commercial service.

Cytochrome p450 is a key catalytic component of the mono-oxygenase system. It constitutes a family of hemoproteins responsible for the oxidative metabolism of xenobiotics (administered drugs), and many endogenous compounds. Different cytochromes present characteristic and overlapping substrate specificity. Most of the biotransforming ability is attributable by the cytochromes designated 1A2, 2A6, 2B6, 3A4, 2C9-11, 2D6, and 2E1 (Gomes-Lechon et al., pp 129-153 in In vitro *Methods in Pharmaceutical Research*, Academic Press, 1997).

A number of assays are known in the art for measuring cytochrome p450 enzyme activity. For example, cells can be contacted with a non-fluorescent substrate that is convertible to a fluorescent product by p450 activity, and then analyzed by fluorescence-activated cell counting (U.S. Pat. No. 5,869, 243). Specifically, the cells are washed, and then incubated with a solution of 10 μM/L 5,6-methoxycarbonylfluorescein (Molecular Probes, Eugene Oreg.) for 15 min at 37° C. in the dark. The cells are then washed, trypsinized from the culture plate, and analyzed for fluorescence emission at ~520-560 nm. p450 enzymes can also be measured in an HPLC-based assay, as illustrated in Example 7. A cell is said to have a specific enzyme activity if the level of activity in a test cell is more than 10-fold, and preferably more than 100- or 1000-fold, above that of a control cell, such as a fibroblast. Mature cells of increasing preference have levels of mature markers within 1000-, 100-, 10- or 2-fold of fetal or adult hepatocytes, or higher, and less than 10-, 100- or 1000-fold of more primitive cells or cells of other tissues.

The expression of cytochrome p450 can also be measured at the protein level, for example, using specific antibody in Western blots, or at the mRNA level, using specific probes and primers in Northern blots or RT-PCR. See Borlakoglu et al., Int. J. Biochem. 25:1659, 1993. Particular activities of the p450 system can also be measured: 7-ethoxycoumarin O-de-ethylase activity, aloxyresorufin O-de-alkylase activity, coumarin 7-hydroxylase activity, p-nitrophenol hydroxylase activity, testosterone hydroxylation, UDP-glucuronyltransferase activity, glutathione S-transferase activity, and others. The activity level can then be compared with the level in primary hepatocytes, as shown in Table 2.

TABLE 2

Drug Metabolizing Activities in 24 hour Primary Cultured Human Hepatocytes

| | Isozyme | Reaction | Activity | |
|---|---|---|---|---|
| Phase I | P450† | | 65 ± 8 | (n = 10) |
| | NADPH-Cc‡ | Cytochrome c oxidation | 23 ± 2 | (n = 10) |
| | CYP1A1/2d§ | Aryl hydrocarbon hydroxylation | 2.93 ± 0.99 | (n = 7) |
| | | 7-Ethoxyresorufin O-de-ethylation | 3.09 ± 2.52 | (n = 14) |
| | CYP2A6§ | Coumarin 7-hydroxylation | 137 ± 42 | (n = 6) |
| | CYP2B6§ | 7-Pentoxyresorufin O-depentylation | 3.28 ± 1.76 | (n = 10) |
| | | 7-Benzoxyresorufin O-debenzylation | 1.38 ± 0.33 | (n = 5) |
| | CYP2C9§ | 4'-Diclofenac hydroxylation | 317 ± 73 | (n = 9) |
| | CYP2E1§ | p-Nitrophenol hydroxylation | 89 ± 42 | (n = 6) |
| | | Chlorzoxazone 6-hydroxylation | 27 ± 3 | (n = 3) |
| | CYP3A3-5§ | Testosterone 6β-hydroxylation | 195 ± 122 | (n = 7) |
| | | Testosterone 2β-hydroxylation | 61 ± 16 | (n = 7) |
| | | Testosterone 15β-hydroxylation | 12.4 ± 8.6 | (n = 7) |
| Phase II | mEH§ | Benzo(a)pyrene 7,8-oxide hydration | 180 ± 72 | (n = 10) |
| | UDPG-t‡ | 4-Methylumbelliferone conjugation | 3.6 ± 0.4 | (n = 5) |
| | GSH-t‡ | 1-Chloro-2,4-dinitrobenzene conjugation | 301 ± 112 | (n = 8) |

*Mean ± s.d. enzymatic activity determined in 24-h cultured human hepatocytes.
†Cytochrome P450 content is expressed as picomoles per milligram of cellular protein.
‡NADPH-C, UDPG-t and GSH-t activities are expressed as nanomoles per milligram per minute.
§CYP enzymatic activities are expressed as picomoles per milligram per minute.

Assays are also available for enzymes involved in the conjugation, metabolism, or detoxification of small molecule drugs. For example, cells can be characterized by an ability to conjugate bilirubin, bile acids, and small molecule drugs, for excretion through the urinary or biliary tract. Cells are contacted with a suitable substrate, incubated for a suitable period, and then the medium is analyzed (by GCMS or other suitable technique) to determine whether a conjugation product has been formed. Drug metabolizing enzyme activities include de-ethylation, dealkylation, hydroxylation, demethylation, oxidation, glucuroconjugation, sulfoconjugation, glutathione conjugation, and N-acetyl transferase activity (A. Guillouzo, pp 411-431 in *In vitro Methods in Pharmaceutical Research*, Academic Press, 1997). Assays include peenacetin de-ethylation, procainamide N-acetylation, paracetamol sulfoconjugation, and paracetamol glucuronidation (Chesne et al., pp 343-350 in *Liver Cells and Drugs*, A. Guillouzo ed. John Libbey Eurotext, London, 1988).

Cells of the hepatocyte lineage can also be evaluated by their ability to store glycogen. A suitable assay uses Periodic Acid Schiff (PAS) stain, which does not react with mono- and disaccharides, but stains long-chain polymers such as glycogen and dextran. PAS reaction provides quantitative estimations of complex carbohydrates as well as soluble and membrane-bound carbohydrate compounds. Kirkeby et al. (Biochem. Biophys. Meth. 24:225, 1992) describe a quantitative PAS assay of carbohydrate compounds and detergents. van der Laarse et al. (Biotech Histochem. 67:303, 1992) describe a microdensitometric histochemical assay for glycogen using the PAS reaction. Evidence of glycogen storage is determined if the cells are PAS-positive at a level that is at least 2-fold, and preferably more than 10-fold above that of a control cell, such as a fibroblast The cells can also be characterized by karyotyping according to standard methods.

A further feature of certain cell populations of this invention is that they are susceptible under appropriate circumstances to pathogenic agents that are tropic for primate liver cells. Such agents include hepatitis A, B, C, and delta, Epstein-Barr virus (EBV), cytomegalovirus (CMV), tuberculosis, and malaria. For example, infectivity by hepatitis B can be determined by combining cultured pPS derived hepatocytes with a source of infectious hepatitis B particles (such as serum from a human HBV carrier). The liver cells can then be tested for synthesis of viral core antigen (HBcAg) by immunohistochemistry or RT-PCR.

The skilled reader will readily appreciate that an advantage of pPS derived hepatocytes is that they will be essentially free of other cell types that typically contaminate primary hepatocyte cultures isolated from adult or fetal liver tissue. Markers characteristic of sinusoidal endothelial cells include Von Willebrand factor, CD4, CD14, and CD32. Markers characteristic of bile duct epithelial cells include cytokeratin-7, cytokeratin-19, and γ-glutamyl transpeptidase. Markers characteristic of stellate cells include α-smooth muscle actin (α-SMA), vimentin, synaptophysin, glial fibrillary acidic protein (GFAP), neural-cell adhesion molecule (N-CAM), and presence of lipid droplets (detectable by autofluorescence or staining by oil red O). Markers characteristic of Kupffer cells include CD68, certain lectins, and markers for cells of the macrophage lineage (such as HLA Class II, and mediators of phagocytosis). pPS derived hepatocytes can be characterized as essentially free of some or all of these cell types if less than 0.1% (preferably less than 100 or 10 ppm) bear markers or other features of the undesired cell type, as determined by immunostaining and fluorescence-activated quantitation, or other appropriate technique.

pPS cells differentiated according to this invention can have a number of the features of the stage of cell they are intended to represent. The more of these features that are present in a particular cell, the more it can be characterized as a cell of the hepatocyte lineage. Cells having at least 2, 3, 5, 7, or 9 of these features are increasingly more preferred. In reference to a particular cell population as may be present in a culture vessel or a preparation for administration, uniformity between cells in the expression of these features is often advantageous. In this circumstance, populations in which at least about 40%, 60%, 80%, 90%, 95%, or 98% of the cells have the desired features are increasingly more preferred.

Other desirable features of differentiated cells of this invention are an ability to act as target cells in drug screening assays, and an ability to reconstitute liver function, both in vivo, and as part of an extracorporeal device. These features are described further in sections that follow.

Matched Cells with Allotypic Differences

The ability to prepare hepatocyte lineage cells from self-renewing pPS cells provides a unique opportunity to generate cells with allotypic differences that are otherwise genetically matched. This is of particular interest in the context of drug metabolism, since the liver plays a pivotal role in maintaining body chemistry, converting or excreting dangerous compounds.

Polymorphisms have been observed in the cytochrome p450 monooxygenases CYP1A2, CYP2C9, CYP2C19; CDP2D6, and CYP2E1 amongst others; as well in other monooxygenases and drug metabolizing enzymes, such as N-acetyltransferase (particularly NAT-2), thioprine methyltransferase, and dihydropyrimidine dehydrogenase. See *Genetic Polymorphism of Drug Metabolizing Enzymes*, E. Tanaka, J. Clin. Pharm. Therapeut. 24:323, 1999; and *Potential Role of Pharmacogenomics in Reducing Adverse Drug Reactions*, Phillips et al., J. Amer. Med. Assoc. 286:2270, 2001. Genetic differences in drug metabolizing enzymes (and other enzymes such as glucose-6-phosphate dehydrogenase) are linked to increased risk of certain diseases such as cancer, and to adverse drug reactions. Most variant alleles are not expressed, or translated into truncated or inactive protein.

Patients who are poor metabolizers or ultrta-rapid metabolizers of different drug classes have been identified and correlated with enzymatic polymorphisms. Dosage requirements for some commonly used drugs with a narrow therapeutic range can differ More than 20-fold, depending on the genotype (Ingelman-Sundberg, Mutat. Res. 482:11, 2001). The p450 enzyme debrisoquine hydroxylase (CYP2D6) metabolizes one quarter of all prescribed drugs and is inactive in 6% of the Caucasian population (Wolf et al., Br. Med. Bull. 55:366, 1999). Polymorphism of mephenytoin (CYP2C19) accounts for variable metabolism of proguanil and some barbiturates, while polymorphism of NAT-2 affects metabolism of hydrazine and aromatic amine drugs such as isoniazid (W. W. Weber, Mol. Diagn. 4:299, 1999).

Matched hepatocyte lineage cells with allotypic differences can be obtained in the following fashion. pPS cells in feeder-free culture are genetically modified according to the techniques described in International Patent Publication WO 01/51616 (Geron Corp.). Modifications are made to a particular p450 component or other drug metabolizing enzyme to alter its function in a manner that makes it resemble a less frequent but naturally occurring allotype. For example, where the naturally occurring variant results in loss of expression or expression of a non-functional protein, then the corresponding gene in pPS cells can simply be modified to remove transcription or translation start signals. Where the natural allotype causes expression of mutant enzyme, then the corresponding gene in pPS cells can be replaced with the mutant form (either by replacing the endogenous gene, or inserting the mutant transgene elsewhere). Homologous recombination using an appropriate targeting vector can achieve any of these changes, but any suitable genetic manipulation technique can be used. The modification can be made in a heterozygous or homozygous fashion.

Cells modified in this way can then be taken through the hepatocyte differentiation paradigm as described earlier. The resulting hepatocytes will have a genome that is identical to those made from the parent pPS line, except for the allotypic difference.

Matched cells are particularly powerful for use in discovery research and screening. They allow the effect of an enzyme polymorphism to be isolated and tested separately, without being subject to other phenotypic differences between the cells.

Other Potential Genetic Modifications

Hepatocyte-like cells of this invention can in principle be obtained in any desired quantity by growing pPS cells to sufficient volume, and then taking them through the hepatocyte differentiation protocol. If desired, the replication capacity can be further enhanced by increasing the level of telomerase reverse transcriptase (TERT), either in the undifferentiated pPS cells, or after differentiation. This can be effected by increasing transcription of TERT from the endogenous gene, or introducing a transgene. Particularly suitable is the catalytic component of human telomerase (hTERT), provided in International Patent Application WO 98/14592. Transfection and expression of telomerase in human cells is described in Bodnar et al., Science 279:349, 1998 and Jiang et al., Nat. Genet. 21:111, 1999. Genetically altered cells can be assessed for hTERT expression by RT-PCR, telomerase activity (TRAP assay), immunocytochemical staining for hTERT, or replicative capacity, according to standard methods. Other methods of immortalizing cells are also contemplated, such as transforming the cells with DNA encoding myc, the SV40 large T antigen, or MOT-2 (U.S. Pat. No. 5,869,243, International Patent Applications WO 97/32972 and WO 01/23555).

If desired, the cells of this invention can be prepared or further treated to remove undifferentiated cells in vitro, or to safeguard against revertants in vivo. One way of depleting undifferentiated stem cells from the population is to transfect the population with a vector in which an effector gene is under control of a promoter that causes preferential expression in undifferentiated cells—such as the TERT promoter or the OCT-4 promoter. The effector gene may be a reporter to guide cell sorting, such as green fluorescent protein. The effector may be directly lytic to the cell, encoding, for example, a toxin, or a mediator of apoptosis, such as caspase. The effector gene may have the effect of rendering the cell susceptible to toxic effects of an external agent, such as an antibody or a prodrug. Exemplary is a herpes simplex thymidine kinase (tk) gene, which causes cells in which it is expressed to be susceptible to ganciclovir (U.S. Pat. No. 6,576,464). Alternatively, the effector can cause cell surface expression of a foreign determinant that makes any cells that revert to an undifferentiated phenotype susceptible to naturally occurring antibody in vivo (GB patent application 0128409.0).

In the context of human therapy, the cells of this invention can be used not just to reconstitute liver function, but also to correct or supplement any other deficiency that is amenable to gene therapy. The cells are modified with a transgene comprising the therapeutic encoding region under control of a constitutive or hematopoietic cell specific promoter, using a technique that creates a stable modification—for example, a retroviral or lentiviral vector, or by homologous recombination. General references include *Stem Cell Biology and Gene Therapy* by P. J. Quesenberry et al. eds., John Wiley & Sons, 1998, which provides a discussion of the therapeutic potential of stem cells as vehicles for gene therapy.

Use of Differentiated Cells

This invention provides a method by which large numbers of cells of the hepatocyte lineage can be produced. These cell populations can be used for a number of important research, development, and commercial purposes.

Expression Libraries, Specific Antibody, and Genomic Analysis

The differentiated cells of this invention can also be used to prepare a cDNA library relatively uncontaminated with cDNA preferentially expressed in cells from other lineages. After reverse transcribing into cDNA, the preparation can be subtracted with cDNA from undifferentiated pPS, embryonic fibroblasts, visceral endoderm, sinusoidal endothelial cells, bile duct epithelium, or other cells of undesired specificity, thereby producing a select cDNA library, reflecting expression patterns that are representative of mature hepatocytes, hepatocyte precursors, or both.

The differentiated cells of this invention can also be used to prepare antibodies that are specific for hepatocyte markers, progenitor cell markers, markers that are specific of hepatocyte precursors, and other antigens that may be expressed on the cells. The cells of this invention provide an improved way of raising such antibodies because they are relatively enriched for particular cell types compared with pPS cell cultures and hepatocyte cultures made from liver tissue. The production of antibodies using pPS derived hepatocytes has been described in WO 01/81549.

Differentiated pPS cells are of interest to identify expression patterns of transcripts and newly synthesized proteins that are characteristic for hepatocyte precursor cells, and may assist in directing the differentiation pathway or facilitating interaction between cells. Expression patterns of the differentiated cells can be obtained and compared with control cell lines, such as undifferentiated pPS cells, using any suitable technique, including but not limited to immunoassay, immunohistochemistry, differential display of mRNA, microarray analysis.

Differentiated pPS Cells for Drug Screening

Differentiated pPS cells of this invention can be used to screen for factors (such as solvents, small molecule drugs, peptides, and polynucleotides) or environmental conditions (such as culture conditions or manipulation) that affect the characteristics of differentiated cells of the hepatocyte lineage.

In some applications, pPS cells (differentiated or undifferentiated) are used to screen factors that promote maturation of cells along the hepatocyte lineage, or promote proliferation and maintenance of such cells in long-term culture. For example, candidate hepatocyte maturation factors or growth factors are tested by adding them to pPS cells in different wells, and then determining any phenotypic change that results, according to desirable criteria for further culture and use of the cells.

Particular screening applications of this invention relate to the testing of pharmaceutical compounds in drug research. The reader is referred generally to the standard textbook *In vitro Methods in Pharmaceutical Research*, Academic Press, 1997, and U.S. Pat. No. 5,030,015). In this invention, pPS cells that have differentiated to the hepatocyte lineage play the role of test cells for standard drug screening and toxicity assays, as have been previously performed on hepatocyte cell lines or primary hepatocytes in short-term culture. Assessment of the activity of candidate pharmaceutical compounds generally involves combining the differentiated cells of this invention with the candidate compound, determining any change in the morphology, marker phenotype, or metabolic activity of the cells that is attributable to the compound (compared with untreated cells or cells treated with an inert compound), and then correlating the effect of the compound with the observed change. The screening may be done either because the compound is designed to have a pharmacological effect on liver cells, or because a compound designed to have effects elsewhere may have unintended hepatic side effects. Two or more drugs can be tested in combination (by combining with the cells either simultaneously or sequentially), to detect possible drug-drug interaction effects.

In some applications, compounds are screened initially for potential hepatotoxicity (Castell et al., pp 375-410 in In vitro *Methods in Pharmaceutical Research*, Academic Press, 1997). Cytotoxicity can be determined in the first instance by the effect on cell viability, survival, morphology, and leakage of enzymes into the culture medium. More detailed analysis is conducted to determine whether compounds affect cell function (such as gluconeogenesis, ureogenesis, and plasma protein synthesis) without causing toxicity. Lactate dehydrogenase (LDH) is a good marker because the hepatic isoenzyme (type V) is stable in culture conditions, allowing reproducible measurements in culture supernatants after 12-24 h incubation. Leakage of enzymes such as mitochondrial glutamate oxaloacetate transaminase and glutamate pyruvate transaminase can also be used. Gomez-Lechon et al. (Anal. Biochem. 236:296, 1996) describe a microassay for measuring glycogen, which can be used to measure the effect of pharmaceutical compounds on hepatocyte gluconeogenesis.

Other current methods to evaluate hepatotoxicity include determination of the synthesis and secretion of albumin, cholesterol, and lipoproteins; transport of conjugated bile acids and bilirubin; ureagenesis; cytochrome p450 levels and activities; glutathione levels; release of α-glutathione s-transferase; ATP, ADP, and AMP metabolism; intracellular $K^+$ and $Ca^{2+}$ concentrations; the release of nuclear matrix proteins or oligonucleosomes; and induction of apoptosis (indicated by cell rounding, condensation of chromatin, and nuclear fragmentation). DNA synthesis can be measured as [$^3$H]-thymidine or BrdU incorporation. Effects of a drug on DNA synthesis or structure can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375-410 in In vitro *Methods in Pharmaceutical Research*, Academic Press, 1997) for further elaboration.

TABLE 3

Desirable Enzyme Specifications for Drug Screening

| Enzyme | Substrate | Catalysis Rate |
|---|---|---|
| CYP3A4 | Testosterone | 66 (5-286) pmol/min/$10^6$ cells |
| CYP2D6 | Dextromethorphan | 23 (2-72) pmol/min/$10^6$ cells |
| CYP2C9 | Tolbutamide | 16 (3-58) pmol/min/$10^6$ cells |
| CYP1A2 | Ethoxyresorufin | 0.13 (0-30.2) pmol/min/$10^6$ cells |
| UDP-GT | Umbelliherone | |
| Sulfo-transferases | Umbelliherone | |

Determining Allotype Dependent Drug Response

In some instances, it will be beneficial to test the effect of particular variants of the p450 system or other enzymes on drug metabolism. Matched pPS derived hepatocytes differing only at a polymorphic locus (engineered as described earlier) are both treated with the test compounds. Effect of the allotype is assessed by comparing results on each cell population, and correlating any difference in the effect with the allotype of the respective population. If desired, the effects of different genetic backgrounds (major haplotypes) on specific variant alleles can be assessed using a representative panel of pPS cells engineered to contain the variant.

This information is valuable in both drug discovery and therapeutic use. Where an allelic variant is associated with altered toxicity or metabolism, therapy can be tailored to particular patient subpopulations. This is done by determining each patient's genotype at the relevant gene loci, and then adjusting the dose or drug type if an incompatible allotype is present. During the discovery phase, it may be possible to identify drugs that are relatively less impacted by phenotypic differences in their toxicity, clearance time, or metabolic profile. The matched cells and techniques described in this disclosure provide an important new system for drug discovery and tailored therapy.

Restoration of Liver Function

This invention also provides for the use of differentiated pPS cells to restore a degree of liver function to a subject needing such therapy, perhaps due to an acute, chronic, or inherited impairment of liver function.

To determine the suitability of differentiated pPS cells for therapeutic applications, the cells can first be tested in a suitable animal model. At one level, cells are assessed for their ability to survive and maintain their phenotype in vivo. Differentiated pPS cells are administered to immunodeficient animals (such as SCID mice, or animals rendered immunodeficient chemically or by irradiation) at a site amenable for further observation, such as under the kidney capsule, into the spleen, or into a liver lobule. Tissues are harvested after a period of a few days to several weeks or more, and assessed as to whether pPS cells are still present. This can be performed by providing the administered cells with a detectable label (such as green fluorescent protein, or β-galactosidase); or by measuring a constitutive marker specific for the administered cells. Where differentiated pPS cells are being tested in a rodent model, the presence and phenotype of the administered cells can be assessed by immunohistochemistry or ELISA using human-specific antibody, or by RT-PCR analysis using primers and hybridization conditions that cause amplification to be specific for human polynucleotide sequences. Suitable markers for assessing gene expression at the mRNA or protein level are provided in elsewhere in this disclosure. General descriptions for determining the fate of hepatocyte-like cells in animal models is provided in Grompe et al. (Sem. Liver Dis. 19:7, 1999); Peeters et al., (Hepatology 25:884, 1997;) and Ohashi et al. (Nature Med. 6:327, 2000).

At another level, differentiated pPS cells re assessed for their ability to restore liver function in an animal lacking full liver function. Braun et al. (Nature Med. 6:320, 2000) outline a model for toxin-induced liver disease in mice transgenic for the HSV tk gene. Rhim et al. (Proc. Natl. Acad. Sci. USA 92:4942, 1995) and Lieber et al. (Proc. Natl. Acad. Sci. USA 92:6210, 1995) outline models for liver disease by expression of urokinase. Mignon et al. (Nature Med. 4:1185, 1998) outline liver disease induced by antibody to the cell-surface marker Fas. Overturf et al. (Human Gene Ther. 9:295, 1998) have developed a model for Hereditary Tyrosinemia Type I in mice by targeted disruption of the Fah gene. The animals can be rescued from the deficiency by providing a supply of 2-(2-nitro-4-fluoro-methyl-benzyol)-1,3-cyclohexanedione (NTBC), but they develop liver disease when NTBC is withdrawn. Acute liver disease can be modeled by 90% hepatectomy (Kobayashi et al., Science 287:1258, 2000). Acute liver disease can also be modeled by treating animals with a hepatotoxin such as galactosamine, $CCl_4$, or thioacetamide.

Chronic liver diseases such as cirrhosis can be modeled by treating animals with a sub-lethal dose of a hepatotoxin long enough to induce fibrosis (Rudolph et al., Science 287:1253, 2000). Assessing the ability of differentiated cells to reconstitute liver function involves administering the cells to such animals, and then determining survival over a 1 to 8 week period or more, while monitoring the animals for progress of the condition. Effects on hepatic function can be determined by evaluating markers expressed in liver tissue, cytochrome p450 activity, and blood indicators, such as alkaline phosphatase activity, bilirubin conjugation, and prothrombin time), and survival of the host Any improvement in survival, disease progression, or maintenance of hepatic function according to any of these criteria relates to effectiveness of the therapy, and can lead to further optimization.

Use in a Liver Assist Device

This invention includes differentiated cells that are encapsulated or part of a bioartificial liver device. Various forms of encapsulation are described in *Cell Encapsulation Technology and Therapeutics*, Kuhtreiber et al. eds., Birkhauser, Boston Mass., 1999. Differentiated cells of this invention can be encapsulated according to such methods for use either in vitro or in vivo.

Bioartificial organs for clinical use are designed to support an individual with impaired liver function—either as a part of long-term therapy, or to bridge the time between a fulminant hepatic failure and hepatic reconstitution or liver transplant. Bioartificial liver devices are reviewed by Macdonald et al., pp. 252-286 of "Cell Encapsulation Technology and Therapeutics", op cit., and exemplified in U.S. Pat. Nos. 5,290,684, 5,624,840, 5,837,234, 5,853,717, and 5,935,849. Suspension-type bioartificial livers comprise cells suspended in plate dialysers, microencapsulated in a suitable substrate, or attached to microcarrier beads coated with extracellular matrix. Alternatively, hepatocytes can be placed on a solid support in a packed bed, in a multiplate flat bed, on a microchannel screen, or surrounding hollow fiber capillaries. The device has an inlet and outlet through which the subject's blood is passed, and sometimes a separate set of ports for supplying nutrients to the cells.

Differentiated pluripotent stem cells are prepared according to the methods described earlier, and then plated into the device on a suitable substrate, such as a matrix of Matrigel® or collagen. The efficacy of the device can be assessed by comparing the composition of blood in the afferent channel with that in the efferent channel—in terms of metabolites removed from the afferent flow, and newly synthesized proteins in the efferent flow.

Devices of this kind can be used to detoxify a fluid such as blood, wherein the fluid comes into contact with the differentiated cells of this invention under conditions that permit the cell to remove or modify a toxin in the fluid. The detoxification will involve removing or altering at least one ligand, metabolite, or other compound (either natural and synthetic) that is usually processed by the liver. Such compounds include but are not limited to bilirubin, bile acids, urea, heme, lipoprotein, carbohydrates, transferrin, hemopexin, asialoglycoproteins, hormones like insulin and glucagon, and a variety of small molecule drugs. The device can also be used to enrich the efferent fluid with synthesized proteins such as albumin, acute phase reactants, and unloaded carrier proteins. The device can be optimized so that a variety of these functions is performed, thereby restoring as many hepatic functions as are needed. In the context of therapeutic care, the device processes blood flowing from a patient in hepatocyte failure, and then the blood is returned to the patient.

Use for Transplantation

Differentiated pPS cells of this invention that demonstrate desirable functional characteristics according to their profile of metabolic enzymes, or efficacy in animal models, may also be suitable for direct administration to human subjects with impaired liver function. For purposes of hemostasis, the cells can be administered at any site that has adequate access to the circulation, typically within the abdominal cavity. For some metabolic and detoxification functions, it is advantageous for the cells to have access to the biliary tract. Accordingly, the cells are administered near the liver (e.g., in the treatment of chronic liver disease) or the spleen (e.g., in the treatment of fulminant hepatic failure). In one method, the cells administered into the hepatic circulation either through the hepatic artery, or through the portal vein, by infusion through an in-dwelling catheter. A catheter in the portal vein can be manipulated so that the cells flow principally into the spleen, or the liver, or a combination of both. In another method, the cells are administered by placing a bolus in a cavity near the target organ, typically in an excipient or matrix that will keep the bolus in place. In another method, the cells are injected directly into a lobe of the liver or the spleen.

The differentiated cells of this invention can be used for therapy of any subject in need of having hepatic function restored or supplemented. Human conditions that may be appropriate for such therapy include fulminant hepatic failure due to any cause, viral hepatitis, drug-induced liver injury, cirrhosis, inherited hepatic insufficiency (such as Wilson's disease, Gilbert's syndrome, or $\alpha_1$-antitrypsin deficiency), hepatobiliary carcinoma, autoimmune liver disease (such as autoimmune chronic hepatitis or primary biliary cirrhosis), and any other condition that results in impaired hepatic function. For human therapy, the dose is generally between about $10^9$ and $10^{12}$ cells, and typically between about $5\times10^9$ and $5\times10^{10}$ cells, making adjustments for the body weight of the subject, nature and severity of the affliction, and the replicative capacity of the administered cells. The ultimate responsibility for determining the mode of treatment and the appropriate dose lies with the managing clinician.

Distribution for Commercial, Therapeutic, and Research Purposes

For purposes of manufacture, distribution, and use, the hepatocyte lineage cells of this invention are typically supplied in the form of a cell culture or suspension in an isotonic excipient or culture medium, optionally frozen to facilitate transportation or storage.

This invention also includes different reagent systems, comprising a set or combination of cells that exist at any time during manufacture, distribution, or use. The cell sets comprise any combination of two or more cell populations described in this disclosure, exemplified but not limited to differentiated pPS-derived cells (hepatocyte lineage cells, their precursors and subtypes), in combination with undifferentiated pPS cells, other pPS derived hepatocytes, or other differentiated cell types. The cell populations in the set sometimes share the same genome or a genetically modified form thereof. Each cell type in the set may be packaged together, or in separate containers in the same facility, or at different locations, at the same or different times, under control of the same entity or different entities sharing a business relationship.

The following examples provided as further non-limiting illustrations of particular embodiments of the invention.

EXAMPLES

Example 1

Differentiation of Human Embryonic Stem Cells Using n-Butyrate

In this experiment, hES cells were maintained on primary mouse embryonic fibroblasts in serum-free medium according to standard methods. Embryoid bodies were formed by harvesting the cells with collagenase for 15-20 min, and plating dissociated clusters onto non-adherent cell culture plates (Costar) in a medium composed of 80% KO DMEM (Gibco) and 20% non-heat-inactivated FBS (Hyclone), supplemented with 1% non-essential amino acids, 1 mM glutamine, 0.1 mM β-mercaptoethanol.

The EBs were fed every other day. After 5 days in suspension culture, they were harvested and plated on Growth Factor Reduced Matrigel® coated plates and in chamber slides (Nunc). One of the following three conditions was used in parallel:
- medium containing 20% fetal bovine serum (FBS);
- medium containing 20% FBS and 5 mM sodium butyrate (Sigma);
- medium containing 20% FBS, 0.5% DMSO (ATCC), 4 μM dexamethazone (Sigma), 150 ng/mL insulin, 10 ng/mL EGF, 600 nM glucagon (Sigma).

In each case, the medium was exchanged every day, and cells were fixed for immunocytochemistry on day 4 after plating.

One day after plating, the EBs plated in 20% FBS alone looked healthy; almost all of them adhered to the plate and appeared to be proliferating. After several days, the cells in FBS alone survived well, and differentiated to form a very heterogeneous population. In contrast, one day after plating, the cultures containing sodium butyrate had a large proportion of apparently dead cells, and only some patches comprising a homogeneous population of cells survived. The morphology of these cells was similar to that of primary hepatocytes, in that the cells were large and became multinucleated after a few days. These cultures compared favorably according to morphological characteristics with cultures of primary human hepatocytes, and with HepG2 cells (a permanent human hepatocyte cell line derived from a hepatoblastoma).

Example 2

Marker Analysis of hES Cell Derived Hepatocytes hES derived embryoid bodies were plated on Matrigel® coated 6-well plates (for RNA extraction) and chamber slides (for immunocytochemistry) in medium containing 20% FBS and 5 mM sodium n-butyrate. The morphology of the differentiated cells was remarkably uniform, showing a large polygonal surface and binucleated center characteristic of mature hepatocytes.

On the sixth day after plating in the differentiation agent, the cells were analyzed for expression of markers by RT-PCR and immunocytochemistry. Glycogen content in these cells was determined using periodic acid Schiff stain. The number of cells in S phase of cell cycle was determined by incubating the cells with 10 μM BrdU on day 5 after plating, and subsequently staining with anti-BrdU antibody 24 hours later.

A summary of the phenotype analysis is provided in Table 4. Albumin expression was found in 55% of the cells. AFP was completely absent. Glycogen was being stored in at least 60% of the cells. 16% of the cells labeled with BrdU, indicating that a significant portion of the cells were proliferating at the time of analysis.

TABLE 4

Phenotype of Differentiated Cells

| Primary Antibody Specificity | % positive cells |
|---|---|
| (none) | 0 |
| non-specific IgG1 | 0 |
| α-fetoprotein | 0 |
| Albumin | 55% |
| α$_1$-antitrypsin | 90% |
| CK18 | 100% |
| CK8 | 100% |
| CK19 | 100% |
| Desmin | 0 |
| Glycogen staining | 60% |
| BrdU staining | 16% |

Real-time PCR amplification (RT-PCR, Taqman™) analysis was performed after six days of culture with n-butyrate, as described previously (WO 01/81549), to look at the expression pattern of various genes normally expressed in hepatocytes. These data were compared with the expression pattern of the same genes in adult hepatocytes, fetal hepatocytes, HepG2 cells (a hepatoblastoma line) and a non-hepatocyte RPE (Retinal pigment epithelial) cell line. Results are shown in Table 5.

TABLE 5

RTPCR analysis of Gene Expression

| | HepG2 hepato-blastoma cell line (positive control) | primary human hepatocytes (positive control) | primary fetal hepatocytes (positive control) | hES cells (undifferentiated) | Embryoid Body cells cultured in FBS (cell mixture) | Embryoid Body cells cultured with DMSO and growth factors | Embryoid Body cells cultured with sodium n-butyrate | RPE epithelial cell line (negative control) |
|---|---|---|---|---|---|---|---|---|
| β-actin | + | + | + | + | + | + | + | + |
| α-fetoprotein | + | + | + | + | + | + | + | − |
| albumin | + | + | + | − | + | + | + | − |
| α$_1$-antitrypsin | + | + | + | − | + | + | + | + |
| HNF1a | + | + | + | − | + | + | − | − |
| HNF3b | + | + | + | − | + | + | − | − |
| HNF4a | + | + | + | − | − | − | − | − |
| ASG receptor | + | + | + | − | + | + | + | − |
| GATA-4 | + | + | + | + | + | + | + | − |
| C/EBPα | + | + | + | − | + | + | + | − |
| C/EBPβ | + | + | + | − | + | + | + | − |

Various analogs of butyrate were also tested at 5 mM. Propionic acid, isovaleric acid, and isobutyric acid were effective in causing hepatocyte differentiation. Trichostatin A, another inhibitor for histone deacetylase, was toxic to cells at 2.5-100 µM, and ineffective at 10-50 nM. At 75-100 nM, Trichostatin A appeared both to induce hepatocyte differentiation, and to select against survival of other cell types.

Example 3

Differentiation of hES to Hepatocyte-Like Cells without Forming Embryoid Bodies

The undifferentiated hES cells were maintained in feeder-free conditions using medium conditioned by mouse embryonic fibroblasts, as previously described (WO 01/51616). The strategy was to initiate a global differentiation process by adding the hepatocyte maturation factors DMSO or retinoic acid (RA) to a subconfluent culture. The cells were then induced to form hepatocyte-like cells by the addition of Na-butyrate.

The hES cells were maintained in undifferentiated culture conditions for 2-3 days after splitting. At this time, the cells were 50-60% confluent and the medium was exchanged with unconditioned SR medium containing 1% DMSO. The cultures were fed daily with SR medium for 4 days and then exchanged into unconditioned SR medium containing 2.5% Na-butyrate. The cultures were fed daily with this medium for 6 days, at which time one half of the cultures were evaluated by immunocytochemistry. The other half of the cultures were harvested with trypsin and replated onto collagen, to further promote enrichment for hepatocyte lineage cells. Immunocytochemistry was then performed on the following day.

As shown in Table 6, the cells which underwent the final re-plating had ~5-fold higher albumin expression, similar $\alpha_1$-antitrypsin expression and 2-fold less cytokeratin expression than the cells not replated. The secondary plating for the cells is believed to enrich for the hepatocyte-like cells.

TABLE 6

Phenotype of Differentiated Cells

| Antibody Specificity | No trypsinization % positive | Trypsinization % positive |
|---|---|---|
| (no primary antibody) | 0 | 0 |
| (IgG1 control) | 0 | 0 |
| albumin | 11% | 63% |
| $\alpha_1$-antitrypsin | >80% | >80% |
| α-fetoprotein | 0 | 0 |
| Cytokeratin 8 | >80% | 45% |
| Cytokeratin 18 | >80% | 30% |
| Cytokeratin 19 | >80% | 30% |
| glycogen | 0 | >50% |

The direct differentiation protocol was adapted to a 4-stage process, as shown in Table 7. Hepatocyte Culture Medium (HCM) was purchased from Clonetics; Strom's Medium is prepared as described in Runge et al., Biochem. Biophys. Res. Commun. 265:376, 1999. The cell populations obtained are assessed by immunocytochemistry and enzyme activity.

TABLE 7

Direct Differentiation Protocols

| Protocol No. | Stage I Undifferentiated cells (until confluent) | Stage II Pre-differentiation (4 days) | Stage III Hepatocyte differentiation (6 days) | Stage IV Hepatocyte maturation (4 days) |
|---|---|---|---|---|
| 7 | Feeder-free conditions | 20% SR medium + 1% DMSO | 20% SR medium + 1% DMSO + 2.5 mM butyrate | HCM + 30 ng/mL hEGF + 10 ng/mL TGF-α + 30 ng/mL HGF + 1% DMSO + 2.5 mM butyrate |
| 8 | Feeder-free conditions | 20% SR medium + 1% DMSO | 20% SR medium + 1% DMSO + 2.5 mM butyrate | 20% SR medium + 30 ng/mL hEGF + 10 ng/mL TGF-α + 30 ng/mL HGF + 1% DMSO + 2.5 mM butyrate |
| 9 | Feeder-free conditions | 20% SR medium + 1% DMSO | 20% SR medium + 1% DMSO + 2.5 mM butyrate | Strom's medium + 30 ng/mL hEGF + 10 ng/mL TGF-α + 30 ng/mL HGF + 1% DMSO + 2.5 mM butyrate |

Other additives tested in the subsequent (4-day) maturation step include factors such as FGF-4 and oncostatin M in the presence of dexamethazone.

In an exemplary experiment, more than 80% of cells in the culture are large in diameter, containing large nuclei and granular cytoplasm. After 5 days in SR medium, the cells were switched to HCM without DMSO. Two days later, many cells were multinucleated, and had a large polygonal shape. By 4 days in HCM, multinucleated polygonal cells were common, having a darker cytosol, resembling freshly isolated human adult hepatocytes or fetal hepatocytes.

FIG. 1 shows the results of another experiment. The differentiation scheme is shown at the top. Micrographs of the cells obtained at the end of Stage IV (middle panel) show a polygonal binucleated phenotype, typical of adult hepatocytes. Immunocytochemistry (lower panel) shows that the cells are positive for albumin, $\alpha_1$-antitrypsin (AT), and cytokeratins 18 and 19 (CK18, CK19), but negative for the early marker α-fetoprotein (AFP). There was also evidence for glycogen storage. All these features mimic features found in adult human hepatocytes.

Example 4

Metabolic Enzyme Activity hES-derived hepatocyte lineage cells generated by the direct differentiation protocol were tested for cytochrome P450 activity.

After completion of the differentiation protocol, cells were cultured for 24-48 hours with or without 5 µM methylchloranthrene, an inducer for the cytochrome P-450 enzymes 1A1 and 1A2 (CYP1A1/2). Enzyme activity was measured as the rate of de-ethylation of ethoxyresorufin (EROD). The substrate was added to the medium at a concentration of 5 µM, and fluorescence of the culture supernatant was measured after 2 hours in a fluorimetric microplate reader at 355 nm excitation and 581 nm emission. The amount of resorufin formed was determined using a standard curve measured for purified resorufin, and expressed as picomoles resorufin formed per min per mg protein.

CYP1A1/2 activity was detected in the three hepatocyte lineage cell lines tested—two derived from the H1 ES cell line, and one derived from the H9 ES cell line. The level of activity was inducible by methylchloranthrene (MC), and exceeded the level observed in two preparations of freshly isolated human adult hepatocytes (HH). The level of activity in undifferentiated H1 and H9 cells (and in the BJ human embryonic fibroblast cell line) was negligible.

The length of time required for differentiated was assessed in a subsequent experiment. hES cells were grown to confluence, pre-differentiated with 1% DMSO in 20% SR medium for 4 days, differentiated in 20% SR medium containing 1% DMSO and 2.5 mM butyrate for various periods, and then matured for 4 days in HCM containing 30 ng/mL hEGF, 10 ng/mL TGF-α, 30 ng/mL HGF, and 2.5 mM butyrate. Levels of p450 enzymes are shown in the following table.

These data suggest that using a differentiation period of 3 days (the short protocol) rather than 6 days (the long protocol) produces hepatocyte-like cells with improved characteristics.

Example 5

Protocol Using Serum Replacement and DMSO without Butyrate

In this alternative method for making hepatocyte lineage cells, the human ES cells were plated at $1\times10^6$ cells per 10 cm well, and grown in mEF conditioned medium containing 8 ng/mL added bFGF for 5 days, changing medium every day.

Stage II/III was conducted by culturing the cells in KO-DMEM containing 20% Serum Replacement (Gibco #10828-028), 2 mM L-glutamine, non-essential amino acids (NEAA), 0.1 mM β-mercaptoethanol, plus 1% DMSO. The medium was changed every day for 7 days.

Stage IV was then started by changing the medium to HCM containing 10 ng/mL EGF plus 2.5 ng/mL HGF. The medium was changed every day for 4 days.

The cells were then replated using trypsin or collagenase without scraping. Collagenase passaging was effected by removing supernatant, and adding 1 mL per well of 1 mg/mL Collagenase IV in KO-DMEM pre-warmed to 37° C. After a 5 min incubation, the collagenase was removed, and the cells were washed with PBS. 1 mL of medium was then added to the well, and the cells were then pipetted vigorously 20-30 times using a P1000 pipette. Under culture conditions where cells did not detach easily, trypsin/EDTA was used instead of collagenase. The washed cells were layered with 0.5 to 1 mL per well (Gibco #25300-054, 0.05% trypsin, 0.53 mM EDTA), and incubated at 37° C. for 5 min. They were then dispersed by repeated pipetting, and the enzyme reaction was quenched with an equal volume of 10% FBS or soybean trypsin inhibitor. Large clumps were left behind, the cells were washed, and pelleted at 1200 rpm

TABLE 8

Enzyme activity in Differentiated hES cells

| | Primary hepatocytes #1 | Primary hepatocytes #2 | *Undifferentiated hES cells | hES derived Hepatocytes: Short Protocol | hES derived Hepatocytes: Long Protocol |
|---|---|---|---|---|---|
| CYP 1A2 | — | — | — | .020 | — |
| CYP 2A6 | 1.724 | 1.584 | — | .270 | .057 |
| CYP 2C19 | 1.107 | 0.268 | .105 | .527 | — |
| CYP 2D6 | 0.764 | 0.786 | .252 | .134 | .354 |
| ECOD | 1.647 | 2.477 | .267 | .142 | .027 |
| UGT | 13.185 | 27.329 | — | 3.964 | — |
| ST | 1.755 | 1.665 | — | .920 | — |
| GST | 16.562 | 18.134 | 9.174 | 46.964 | 21.208 |
| Uninduced EROD activity | 0 | 0 | 0 | 0.5 ± 0.1 | 0.3 ± 0.1 |
| Induced EROD activity | 3.2 ± 1.2 | 0.4 ± 0.0 | 0.7 ± 0.0 | 1.6 ± 0.5 | 0.8 ± 0.1 |

CYP 1A2 = 7-ethoxyresorufin O-deethylation
CYP 2A6 = coumarin 7-hydrozylation
CYP 2C19 = S-mephenytoin 4'-hydroxylation
CYP 2D6 = dextromethorphan O-demethylation
ECOD = 7-ethoxycoumarin O-deethylation
UGT = 7-hydroxycoumarin glucuronidation
ST = 7-hydroxycoumarin sulfation
GST = conjugation of reduced glutathione with 1-chloro-2,4,dinitrobenzene
EROD = de-ethylation of ethoxyresorufin (Units: nM EROD catalyzed per hour per $10^6$ cells)
"—" indicates no determination was made.

for 10 min. The cells were then suspended in new medium, and plated onto a 6 well plate.

FIG. 2 (top) shows the differentiation scheme up to this point. The cells were replated at ~0.2 to 1×10$^6$ cells per well, and grown for 15 days or until the wells looked confluent., changing the medium every 2-3 days. The cells were then matured by culturing in the same medium containing 1 µM dexamethazone, plus either 10 ng/mL HGF or 10 ng/mL EGF, changing the medium every 2-3 days. The middle panel shows the cells after ~15 days, demonstrating morphology characteristic of hepatocytes.

The lower panel shows analysis of expression of hepatocyte lineage markers, detected by real-time PCR, and normalized to the level expressed by samples of human adult liver. As cells pass through the maturation steps, the level of mRNA in the culture for cytochrome p450 enzymes CYP3A4, CYP3A7, and the p450 regulator PXR rise to a level that is closer to intact liver. Activity of CYP3A4 measured in an enzyme assay (Example 7) was activated by rifampicin, and inhibited by ketoconozole, which is typical of natural CYP3A4 activity.

Example 6

Growth Factor Protocol

In this alternative method for making hepatocyte lineage cells, the human ES cells were plated at 1×10$^6$ cells per 10 cm well, and grown in mEF conditioned medium containing 8 ng/mL added bFGF for 5 days, changing medium every day.

Stage II was conducted by culturing the cells in KO-DMEM containing 20% Serum Replacement (Gibco #10828-028), 2 mM L-glutamine, NEAA 1×, β-mercaptoethanol, plus 1% DMSO. The medium was changed every day for 4 days.

For Stage III, the cells were cultured in HCM (Clonetics), containing 2.5 ng/mL HGF plus 0.1 µM dexamethazone, changing the medium every day for 3 days For Stage IV, the medium was changed to HCM containing 10 ng/mL EGF, 2.5 ng/mL HGF, 0.1 µM dexamethazone, plus 1% DMSO. The medium was changed daily for 4 days.

The cells were then replated as already described at ~0.2 to 1×10$^6$ cells per well. They were grown for 15 days or until the wells looked confluent. They were then matured by culturing in a medium containing 10 ng/mL HGF, plus 1 µM dexamethazone with or without 10 ng/mL oncostatin M. After ~15 days of culture, the cells had morphology characteristic of hepatocytes.

Morphology, gene expression, and enzyme analysis was similar for the cells obtained by this procedure as for those in Example 5.

Example 7

Endoderm Protocol

This method of producing pPS-derived hepatocytes follows the natural ontological pathway of liver cells through formation of primitive endoderm.

In Stage I, ES cells are seeded onto the plates at 1×10$^6$ cells per 10 cm well, and grown in mEF conditioned medium containing 8 ng/mL added bFGF for 3 days, changing medium every day. The cells are then cultured in Medium B, which is DMEM containing 1 mM L-glutamine and 10% FBS for 4.5 days, changing the medium daily; and then for 12 hours in the same medium containing 10 ng/mL FGF-8. The cells are passaged using 1 mL 0.05% trypsin per well for 5 min at 37° C., which is then quenched with 1 mL FBS in 3 mL Medium B.

In Stage II, plates are precoated with gelatin by incubating with 0.5% gelatin overnight at 37° C. The cells are plated onto the gelatin coated plates or onto a feeder layer at 0.8×10$^6$ cells per 10 cm$^2$ well, and then cultured for 3 days in Medium B containing 10 ng/mL bFGF. They are then cultured for 2 days in HCM containing 5 ng/mL each of BMP-2, BMP-4, and BMP-6, and also 1 µM dexamethasone.

In Stage III, the cells are cultured in HCM containing the same concentration of BMPs and dexamethasone, plus 10 ng/mL Oncostatin M for 2 days, and then in HCM containing BMPs, dexamethasone, Oncostatin M, plus 20 ng/mL nerve growth factor (NGF).

In Stage IV, the cells are cultured for 10 days in HCM containing 1 µM dexamethasone, 20 ng/mL NGF, and 10 ng/mL HGF.

FIG. 3 (bottom panel) shows the morphology of the culture at various points in the differentiation process. IN early experiments, the protocol was carried out on a layer of irradiated mesenchymal stem cells, present as a feeder layer. It was later discovered that the feeders could be replaced by gelatin, or an equivalent substrate or extracellular matrix on the vessel surface.

FIG. 4 shows some useful markers for various stages of differentiation.

FIG. 5 (top panel) shows expression of Hex (an early marker) by Stage I cells of this protocol, and ApoCII and tyrosine oxidase (TO) (both late markers) by Stage III and IV cells, as detected by RT-PCR. The bottom panel shows expression of CYP3A4 and the regulator PXR as measured by RT-PCR.

Figure 6:
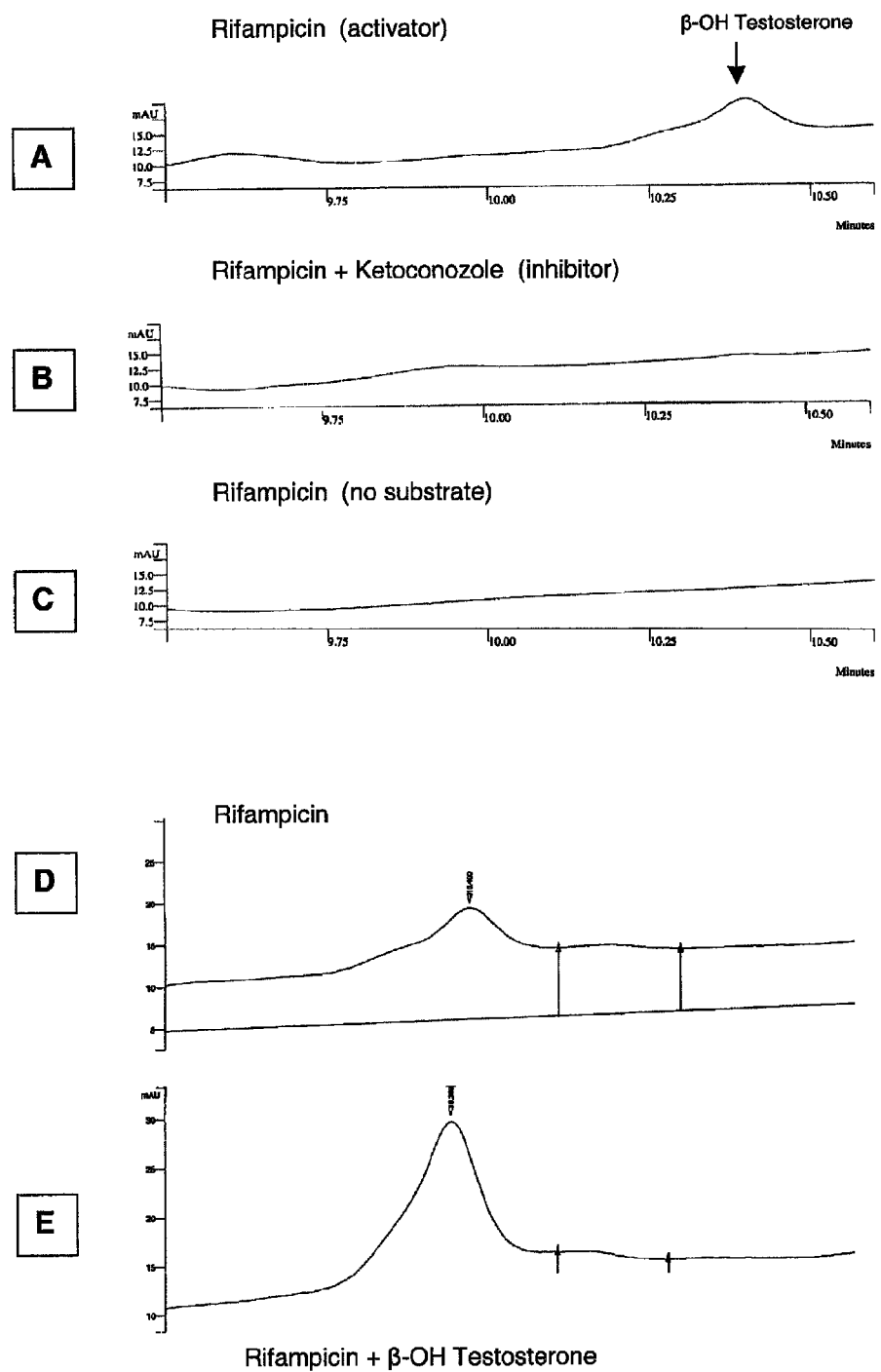

FIG. 6 shows results of a CYP3A4 enzyme assay conducted on cells harvested following Stage IV. Unlabeled substrate and product were separated by HPLC, and detected by inherent light absorption. Kostrubsky et. al., Drug Metab. Dispos. 27:887, 1999; Li, A. P. Chapter 13 in *Handbook of Drug Screening*, Seethala & Fernandes Eds., Marcel Dekker, 2001.

In Panel A, cells were pretreated with the CYP3A4 inducer rifampicin, and then administered the substrate testosterone. The tracing shows the $A_{242}$ absorbance profile of the HPLC eluant. A peak appeared at an elution volume corresponding to the expected reaction product, β-hydroxy testosterone. Absence of the substrate (Panel C), or presence of the inhibitor ketoconozole (Panel B), blocks appearance of the β-OH testosterone peak. Panel D shows an expanded tracing of the β-OH testosterone peak produced by cells induced with rifampicin. In Panel E, the product of the induced cells was spiked with β-OH testosterone, confirming the position of the reaction product.

These data support the proposition that there are phenotypic characteristics and p450 enzyme activity in the hES cell derived hepatocytes that make them resemble adult hepatocytes in a way that validates their use for drug screening and clinical therapy.

It is understood that certain adaptations of the invention are a matter of routine optimization, and can be implemented without departing from the spirit of the claimed invention

The invention claimed is:

1. A method for screening for a response of cultured hepatocyte lineage cells to an administered chemical compound, the method comprising: a) obtaining a population of cultured cells that are in vitro differentiated progeny of cells expressing SSEA3, SSEA4, TRA-1-60 and TRA-1-81 and have morphological features of hepatocytes; b) administering the chemical compound to the population of cultured cells; and c) measuring a response of the population of cultured cells to the administered compound; wherein the response is selected from a change in the viability, survival, morphology, marker phenotype, metabolic activity, and/or leakage of enzymes into the culture medium of the cultured cells.

2. The method of claim 1, further comprising: d) obtaining a second population of cultured cells that are in vitro differentiated progeny of cells expressing SSEA3, SSEA4, TRA-1-60 and TRA-1-81 and have morphological features of hepatocytes; wherein the second population of cultured cells are genetically identical to the population of cultured cells of claim 1, except for a difference at a single polymorphic locus that encodes a drug metabolizing enzyme; e) administering the chemical compound to the second population of cultured cells; and f) measuring a response of the second population of cultured cells to the administered compound; wherein the response is the same response measured in c).

3. The method of claim 2, wherein the single polymorphic locus is associated with altered toxicity or metabolism.

4. The method of claim 3, wherein the single polymorphic locus encodes a cytochrome P450 enzyme.

5. The method of claim 1, wherein the response is a change in the viability of the cultured cells.

6. The method of claim 1, wherein the response is a change in the survival of the cultured cells.

7. The method of claim 1, wherein the response is a change in the morphology of the cultured cells.

8. The method of claim 1, wherein the response is a change in the marker phenotype of the cultured cells.

9. The method of claim 1, wherein the response is a change in the metabolic activity of the cultured cells.

10. The method of claim 1, wherein the response is a change in the leakage of enzymes into the culture medium of the cultured cells.

* * * * *